United States Patent
Shimada et al.

(10) Patent No.: US 10,338,039 B2
(45) Date of Patent: Jul. 2, 2019

(54) METHOD FOR DETECTING MONOCLONAL ANTIBODY USING MASS SPECTROMETRY

(71) Applicant: SHIMADZU CORPORATION, Kyoto-shi (JP)

(72) Inventors: Takashi Shimada, Kyoto (JP); Noriko Iwamoto, Kyoto (JP)

(73) Assignee: SHIMADZU CORPORATION, Kyoto-shi (JP)

( * ) Notice: Subject to any disclaimer, the term of this patent is extended or adjusted under 35 U.S.C. 154(b) by 0 days.

(21) Appl. No.: 15/556,018

(22) PCT Filed: Dec. 18, 2015

(86) PCT No.: PCT/JP2015/085445
§ 371 (c)(1),
(2) Date: Sep. 6, 2017

(87) PCT Pub. No.: WO2016/143224
PCT Pub. Date: Sep. 15, 2016

(65) Prior Publication Data
US 2018/0059074 A1  Mar. 1, 2018

(30) Foreign Application Priority Data

Mar. 9, 2015 (JP) ................. 2015-046059

(51) Int. Cl.
G01N 27/62 (2006.01)
G01N 30/06 (2006.01)
G01N 30/72 (2006.01)
G01N 30/88 (2006.01)
G01N 33/68 (2006.01)

(52) U.S. Cl.
CPC ......... *G01N 30/7233* (2013.01); *G01N 27/62* (2013.01); *G01N 30/06* (2013.01); *G01N 30/88* (2013.01); *G01N 33/68* (2013.01); *G01N 33/6857* (2013.01); *G01N 30/72* (2013.01); *G01N 2030/8818* (2013.01); *G01N 2030/8831* (2013.01); *G01N 2560/00* (2013.01)

(58) Field of Classification Search
CPC .... G01N 30/7233; G01N 30/88; G01N 33/68; G01N 33/6857
See application file for complete search history.

(56) References Cited

U.S. PATENT DOCUMENTS

2016/0252522 A1    9/2016  Shimada et al.
2018/0052172 A1*   2/2018  Shimada .............. G01N 30/06
2019/0011455 A1*   1/2019  Lebert ................. G01N 33/502

FOREIGN PATENT DOCUMENTS

JP   2010-515020 A   5/2010
JP   2012-197258 A   10/2012
WO   2008/079914 A1  7/2008
WO   2015/033479 A1  3/2015

OTHER PUBLICATIONS

International Search Report dated Mar. 1, 2016 in PCT/JP2015/085445 filed Dec. 18, 2015.

N. Leigh Anderson et al., "Mass Spectrometric Quantitation of Peptides and Proteins Using Stable Isotope Standards and Capture by Anti-Peptide Antibodies (SISCAPA)", Journal of Proteome Research, 2004, vol. 3, No. 2, pp. 235-244.

Qianhao Min et al., "Size-selective proteolysis on mesoporous silica-based trypsin nanoreactor for low-MW proteome analysis", Chemical Communications, 2010, vol. 46, pp. 6144-6146.

Fei Xu et al., "Facile Trypsin Immobilization in Polymeric Membranes for Rapid, Efficient Protein Digestion", Analytical Chemistry, Dec. 15, 2010, vol. 82, No. 24, pp. 10045-10051.

Xiaotao Duan et al., "High-Throughput Method Development for Sensitive, Accurate, and Reproducible Quantification of Therapeutic Monoclonal Antibodies in Tissues Using Orthogonal Array Optimization and Nano Liquid Chromatography/Selected Reaction Monitoring Mass Spectrometry", Analytical Chemistry, 2012, vol. 84, pp. 4373-4382.

Noriko Iwamoto et al., "Selective detection of complementarity-determining regions of monoclonal antibody by limiting protease access to the substrate: nano-surface and molecular-orientation limited proteolysis", Analyst, Feb. 7, 2014, vol. 139, 22 total pages.

European Search Report dated Dec. 7, 2018, in corresponding application No. 15884708.7.

(Continued)

*Primary Examiner* — Marcela M Cordero Garcia

(74) *Attorney, Agent, or Firm* — Oblon, McClelland, Maier & Neustadt, L.L.P.

(57) ABSTRACT

A method is provided for more easily detecting and quantifying a protein by regioselectively digesting a variable region of an Fab domain of a monoclonal antibody while suppressing proteolysis of an Fc domain.

In the method, a porous body in which a monoclonal antibody is immobilized in pores and nanoparticles on which a protease is immobilized are brought into contact with each other in a liquid to perform selective proteolysis of the monoclonal antibody, and a resulting peptide fragment is detected using liquid chromatography-mass spectrometry (LC-MS), and a peptide having an amino acid sequence that includes an amino acid derived from a CDR2 region of a heavy chain or a light chain of the monoclonal antibody is detected.

13 Claims, 6 Drawing Sheets

Specification includes a Sequence Listing.

(56) References Cited

OTHER PUBLICATIONS

Qian Zhang, et al., "Generic Automated Method for Liquid Chromatography-Multiple Reaction Monitoring Mass Spectrometry Based Monoclonal Antibody Quantitation for Preclinical Pharmacokinetic Studies", Analytical Chemistry vol. 86 (17) pp. 8776-8784 (2014).
R. W. Kondrat, et al, "Multiple Reaction Monitoring in Mass Spectrometry /Mass Spectrometry for Direct Analysis of Complex Mixtures", Analytical Chemistry, Vol. 50. No. 14, Dec. 1978 • 2017.

* cited by examiner

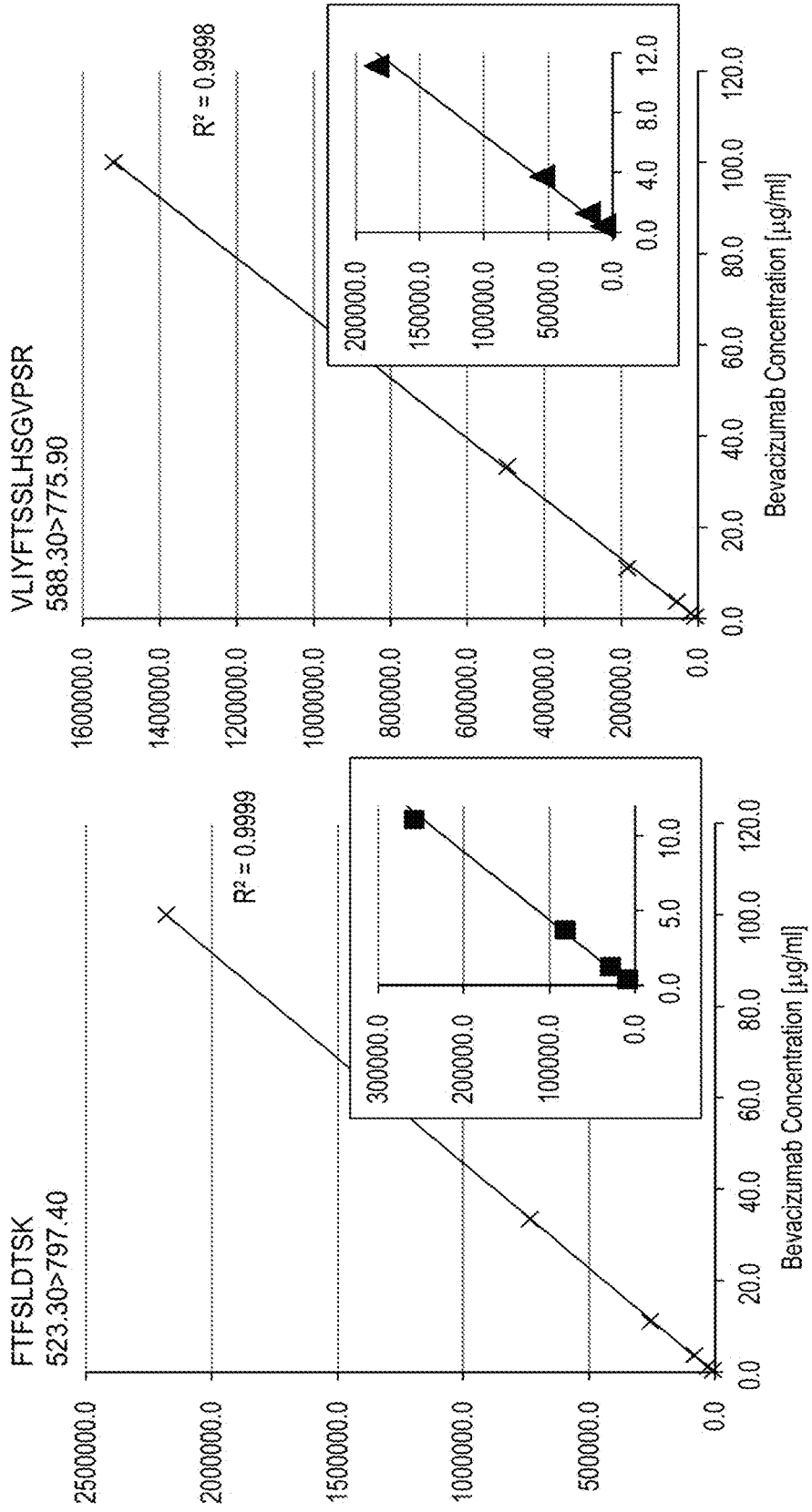

```
                       SEQUENCE LISTING

<160> NUMBER OF SEQ ID NOS: 19

<210> SEQ ID NO 1
<211> LENGTH: 9
<212> TYPE: PRT
<213> ORGANISM: Artificial
<220> FEATURE:
<223> OTHER INFORMATION: antibody fragment

<400> SEQUENCE: 1

Ile Tyr Pro Thr Asn Gly Tyr Thr Arg
1               5

<210> SEQ ID NO 2
<211> LENGTH: 11
<212> TYPE: PRT
<213> ORGANISM: Artificial
<220> FEATURE:
<223> OTHER INFORMATION: antibody fragment

<400> SEQUENCE: 2

Ala Glu Asp Thr Ala Val Tyr Tyr Cys Ser Arg
1               5                   10

<210> SEQ ID NO 3
<211> LENGTH: 9
<212> TYPE: PRT
<213> ORGANISM: Artificial
<220> FEATURE:
<223> OTHER INFORMATION: antibody fragment

<400> SEQUENCE: 3

Phe Thr Ile Ser Ala Asp Thr Ser Lys
1               5

<210> SEQ ID NO 4
<211> LENGTH: 11
<212> TYPE: PRT
<213> ORGANISM: Artificial
<220> FEATURE:
<223> OTHER INFORMATION: antibody fragment

<400> SEQUENCE: 4

Leu Ser Cys Ala Ala Ser Gly Phe Asn Ile Lys
1               5                   10

<210> SEQ ID NO 5
<211> LENGTH: 8
<212> TYPE: PRT
<213> ORGANISM: Artificial
<220> FEATURE:
<223> OTHER INFORMATION: antibody fragment
```

```
<400> SEQUENCE: 5

Asp Thr Tyr Ile His Trp Val Arg
1               5

<210> SEQ ID NO 6
<211> LENGTH: 7
<212> TYPE: PRT
<213> ORGANISM: Artificial
<220> FEATURE:
<223> OTHER INFORMATION: antibody fragment

<400> SEQUENCE: 6

Gly Leu Glu Trp Val Ala Arg
1               5

<210> SEQ ID NO 7
<211> LENGTH: 11
<212> TYPE: PRT
<213> ORGANISM: Artificial
<220> FEATURE:
<223> OTHER INFORMATION: antibody fragment

<400> SEQUENCE: 7

Asn Thr Ala Tyr Leu Gln Met Asn Ser Leu Arg
1               5                   10

<210> SEQ ID NO 8
<211> LENGTH: 11
<212> TYPE: PRT
<213> ORGANISM: Artificial
<220> FEATURE:
<223> OTHER INFORMATION: antibody fragment

<400> SEQUENCE: 8

Ala Glu Asp Thr Ala Val Tyr Tyr Cys Ala Lys
1               5                   10

<210> SEQ ID NO 9
<211> LENGTH: 11
<212> TYPE: PRT
<213> ORGANISM: Artificial
<220> FEATURE:
<223> OTHER INFORMATION: antibody fragment

<400> SEQUENCE: 9

Ser Thr Ala Tyr Leu Gln Met Asn Ser Leu Arg
1               5                   10

<210> SEQ ID NO 10
<211> LENGTH: 9
<212> TYPE: PRT
<213> ORGANISM: Artificial
<220> FEATURE:
<223> OTHER INFORMATION: antibody fragment

<400> SEQUENCE: 10

Phe Thr Phe Ser Leu Asp Thr Ser Lys
1               5

<210> SEQ ID NO 11
<211> LENGTH: 16
<212> TYPE: PRT
<213> ORGANISM: Artificial
<220> FEATURE:
<223> OTHER INFORMATION: antibody fragment
```

```
<400> SEQUENCE: 11

Val Leu Ile Tyr Phe Thr Ser Ser Leu His Ser Gly Val Pro Ser Arg
1               5                   10                  15

<210> SEQ ID NO 12
<211> LENGTH: 19
<212> TYPE: PRT
<213> ORGANISM: Artificial
<220> FEATURE:
<223> OTHER INFORMATION: antibody fragment

<400> SEQUENCE: 12

Leu Ser Cys Ala Ala Ser Gly Tyr Thr Phe Thr Asn Tyr Gly Met Asn
1               5                   10                  15

Trp Val Arg

<210> SEQ ID NO 13
<211> LENGTH: 7
<212> TYPE: PRT
<213> ORGANISM: Artificial
<220> FEATURE:
<223> OTHER INFORMATION: antibody fragment

<400> SEQUENCE: 13

Ala Thr Leu Thr Ala Asp Lys
1               5

<210> SEQ ID NO 14
<211> LENGTH: 6
<212> TYPE: PRT
<213> ORGANISM: Artificial
<220> FEATURE:
<223> OTHER INFORMATION: antibody fragment

<400> SEQUENCE: 14

Val Thr Met Thr Cys Arg
1               5

<210> SEQ ID NO 15
<211> LENGTH: 8
<212> TYPE: PRT
<213> ORGANISM: Artificial
<220> FEATURE:
<223> OTHER INFORMATION: antibody fragment

<400> SEQUENCE: 15

Leu Ala Ser Gly Val Pro Val Arg
1               5

<210> SEQ ID NO 16
<211> LENGTH: 12
<212> TYPE: PRT
<213> ORGANISM: Artificial
<220> FEATURE:
<223> OTHER INFORMATION: antibody fragment

<400> SEQUENCE: 16

Ala Thr Ser Asn Leu Ala Ser Gly Val Pro Val Arg
1               5                   10

<210> SEQ ID NO 17
<211> LENGTH: 16
<212> TYPE: PRT
<213> ORGANISM: Artificial
<220> FEATURE:
<223> OTHER INFORMATION: antibody fragment
```

```
<400> SEQUENCE: 17

Phe Ser Gly Ser Gly Ser Gly Thr Ser Tyr Ser Leu Thr Ile Ser Arg
1               5                   10                  15

<210> SEQ ID NO 18
<211> LENGTH: 15
<212> TYPE: PRT
<213> ORGANISM: Artificial
<220> FEATURE:
<223> OTHER INFORMATION: antibody fragment

<400> SEQUENCE: 18

Ala Ser Gly Tyr Thr Phe Thr Ser Tyr Asn Met His Trp Val Lys
1               5                   10                  15

<210> SEQ ID NO 19
<211> LENGTH: 14
<212> TYPE: PRT
<213> ORGANISM: Artificial
<220> FEATURE:
<223> OTHER INFORMATION: antibody fragment

<400> SEQUENCE: 19

Ala Ser Ser Ser Val Ser Tyr Ile His Trp Phe Gln Gln Lys
1               5                   10
```

METHOD FOR DETECTING MONOCLONAL ANTIBODY USING MASS SPECTROMETRY

TECHNICAL FIELD

The present invention relates to a method for detecting a monoclonal antibody using mass spectrometry, and more specifically relates to a method that includes a preprocessing step in which a peptide fragment that includes a specific sequence of a monoclonal antibody is selectively digested, and a step in which a resulting peptide fragment is selectively detected.

TECHNICAL BACKGROUND

A biggest challenge in the field of drug discovery is development of drugs that exhibit high medicinal effects with few side effects. Therefore, currently being focused on is pharmacokinetics, in particular, concentration monitoring (therapeutic drug monitoring, TDM). Screening of seeds is performed based on whether or not a prescribed medicine is of an adequate amount and whether or not the medicine reaches a lesion site as indicators, and thereby, drugs to drop out are discovered at an early stage, and this information can be effectively used in early drug discovery development and clinical trials. In particular, in fields such as cancer and autoimmune diseases, drug discovery called molecularly targeted drugs is mainstream these days. It is important that an effective pharmacological effect of a molecularly targeted drug can be judged by a doctor himself or herself by measuring whether or not the drug accumulates at a lesion site and exerts its medicinal effect.

Currently, antibody drugs that use a pathogenic protein as a target antigen are attracting attention as molecularly targeted drugs. Since an antibody is a protein that naturally present in the body, side effects are expected to be low, and it is also possible to administer an antibody at a high concentration to enhance a molecular target effect. Further, due to its nature, an antibody has been said to exhibit extremely high molecular specificity and accumulate in a target lesion. However, there is also a problem of drug prices of antibody drugs, and it is argued that it is important to conduct optimized medical care by proper use of antibody drugs. Therefore, it is also important to set an optimal dosage by measuring localization and concentration of an antibody drug. Further, there is also a great demand for quantification of concentration of an antibody drug in order to proper observe a drug efficacy indicator of an administered drug.

A most common technique for quantification of a protein such as an antibody is ELISA (Enzyme-Linked ImmunoSorbent Assay). This is a technique for easily quantifying molecules to be measured by preparing an antibody with respect to a protein to be measured and further sandwiching with detection antibodies. ELISA is an extremely versatile technology and an automated support environment is also in place. Therefore, ELISA is expected to become a golden standard as a diagnostic technology from now on.

However, for example, ELISA does not directly measure a target to be measured. Therefore, there are many problems such as that an abnormal value may be generated, that it takes time and cost since it is necessary to produce an antibody for each target to be measured, and that it is impossible to simultaneously measure multiple analysis targets. In particular, for an antibody drug, a cross reaction with an endogenous antibody also occurs, and thus an accurate measurement is difficult. Further, in a state in which a neutralizing antibody and an antigen are bound to each other, an antigen recognition site is blocked and it is often not possible to perform measurement using ELISA.

Further, under analysis conditions of ELISA adopted in an animal test phase, due to a problem of interspecific crossing, it is often not directly applicable to large animals and humans. That is, in a drug discovery development stage and in a human clinical trial, it is inevitable to perform comparison under separate measurement conditions. In ELISA of a drug concentration in a lesion tissue, matrix components that inhibit detection are different. Therefore, in order to perform pharmacokinetics based on ELISA, it is necessary to prepare multiple antibodies. This has a very large risk such as enormous cost and dropout in late-stage development.

On the other hand, quantitative and structural analysis of proteins using mass spectrometry has been dramatically expanded in its application range, along with developments of mass spectrometry technologies and data analysis server and software. In particular, an absolute quantification technique using mass spectrometry has increased awareness as a method independent of specific antibodies.

For example, when quantifying a protein without a commercially available antibody, conventionally, it was necessary to purify the protein in a large amount. However, by using mass spectrometry, this step is omitted and thus it becomes dramatically efficient. Even in the field of medicine, conventionally, due to problems such as procedures of doctors such as a method for thin sectioning of a pathological section and a method of preservation, a difference occurs in immunohistochemical staining, and it is often difficult to judge positivity, false positivity, and negativity. In contrast, by quantifying a target pathogenic protein in a pathological section using mass spectrometry, it is possible to judge whether or not the protein is a highly expressed protein. Further, in recent years, a device called a laser microdissection that cuts out one cell is generically used. For example, it is possible to collect only cancer cells and directly observe expression variation analysis of a pathogenic protein in the cells using mass spectrometry. This is a very innovative technological innovation, especially in pathology and in clinical practice, and preparation such as standardization of analytical techniques is desired.

While it is a highly accurate analytical technique, when a protein in a biological sample is detected using mass spectrometry, a protein to be measured is often fragmented by proteolysis. Therefore, it is important to efficiently select a target peptide fragment from various peptide fragments including contaminants.

Patent Document 1 discloses that, in order to detect an antibody in a sample, an F(ab')2 fragment is produced by using pepsin to decompose a non-immunoglobulin protein and digest an antibody, and thereafter, trypsin digestion is further performed. Further, Patent Document 2 discloses that only a peptide appropriately separated at a liquid chromatography stage prior to mass spectrometry is selected as a quantification target. Non-Patent Document 1 discloses that an anti-peptide antibody is used to concentrate a peptide to be measured.

Further, in recent years, as a method for improving efficiency of protease digestion, a method has attracted attention in which protease digestion is performed in a microenvironment (microreactor) such as a nanoparticle. For example, Non-Patent Document 2 reports that, by using mesoporous silica in which trypsin is immobilized in the pores, it is possible to selectively trypsin digest a protein with a small molecular weight. Non-Patent Document 3 reports an example in which trypsin is immobilized on a nylon membrane and high efficiency of trypsin digestion of a protein is achieved. In all of these methods, a protease is immobilized in pores of a porous body, and the protease on a solid surface and a substrate protein in a liquid phase are caused to react.

Non-Patent Document 4 proposes a high-throughput method for identifying a monoclonal antibody and an endogenous antibody in a sample.

RELATED ART

Patent Documents

[Patent Document 1] Japanese Translation of PCT International Application Publication No. 2010-515020.
[Patent Document 2] Japanese Patent Laid-Open Publication No. 2012-197258.

Non-Patent Documents

[Non-Patent Document 1] N. Leigh Anderson at. al, Mass Spectrometric Quantitation of Peptides and Proteins Using Stable Isotope Standards and Capture by Anti-Peptide Antibodies (SISCAPA), Journal of Proteome Research, 2004, 3 (2), 235.
[Non-Patent Document 2] Qianhao Min at. al., Size-selective proteolysis on mesoporous silica-based trypsin nanoreactor for low-MW proteome analysis, Chemical Communications, 2010, 46, 6144.
[Non-Patent Document 3] Fei Xu at. al., Facile Trypsin Immobilization in Polymeric Membranes for Rapid, Efficient Protein Digestion, Analytical Chemistry, Analytical Chemistry, 2010, 82, 10045.
[Non-Patent Document 4] Xiaotao Duan at. al., High-Throughput Method Development for Sensitive, Accurate, and Reproducible Quantification of Therapeutic Monoclonal Antibodies in Tissues Using Orthogonal Array Optimization and Nano Liquid Chromatography/Selected Reaction Monitoring Mass Spectrometry, Analytical Chemistry, 2012, 84, 4373.

SUMMARY OF THE INVENTION

Problems to be Solved by the Invention

In order to easily detect and quantify a protein using a mass spectrometry method, it is required to regioselectively cut a protein to be measured, efficiently produce a peptide fragment specific to the protein, and reduce a production amount of other peptide fragments. Therefore, in a case of an antibody, it is necessary to regioselectively digest an Fab domain, especially a variable region of an Fab domain, while suppressing digestion of an Fc domain.

A group including the present inventors was able to realize regioselective proteolysis of a monoclonal antibody by immobilizing both an antibody serving as a substrate and a protease enzyme on a solid phase (N. Iwamoto at. al., Selective detection of complementarity determining regions of monoclonal antibody by limiting protease access to the substrate: nano-surface and molecular-orientation limited proteolysis, Analyst, 2014, 139, 576). In this method, a porous body in which a monoclonal antibody to be measured is immobilized in pores and nanoparticles on which a protease is immobilized are brought into contact with each other in a liquid to perform selective proteolysis of the monoclonal antibody, and a resulting peptide fragment is detected using liquid chromatography-mass spectrometry (LC-MS). It is reported that, as a protease, double digestion using trypsin and lysyl endopeptidase (Lys-C) at a ratio of 9:1 is most efficient.

Although the above method is an innovative method for performing selective proteolysis of a monoclonal antibody using a solid phase-solid phase reaction, in order to actually use the method, there is room for further consideration.

Therefore, objects of the present invention are:
to more easily prepare a peptide having a specific amino acid sequence contained in an antibody based on a higher order structure of the antibody;
to save labor and allow generalization by omitting a preprocessing process (denaturation, reductive alkylation) used in proteomics and performing decomposition under a physiological condition;
to maintain the specificity of a sample while reducing the number of populations of analytical peptides;
to establish a general analysis method adaptable to diversity of antibody drugs and capable of overcoming a cross reaction between species and a coexistence matrix of derived samples; and
to ensure specificity even for a sample in which matrix components such as blood and tissue coexist.

Means for Solving the Problems

As a result of intensive studies in consideration of the above problems, the present inventors have found that, in order to detect an antibody using limiting proteolysis of the present invention, it is most effective to detect a proteolysis fragment contained in particular in a CDR2 region in a variable region of a monoclonal antibody, and thus accomplished the present invention.

That is, the present invention includes the following aspects.

(1) A method is provided in which a porous body in which a monoclonal antibody to be measured is immobilized in pores and nanoparticles on which a protease is immobilized are brought into contact with each other in a liquid to perform selective proteolysis of the monoclonal antibody; a resulting peptide fragment is detected using liquid chromatography-mass spectrometry (LC-MS); the porous body has an average pore diameter in a range of 10 nm-200 nm; the nanoparticles have an average particle size in a range of 50 nm-500 nm; the average particle size of the nanoparticles is larger than the average pore diameter of the porous body; and a peptide fragment to be detected has an amino acid sequence that includes an amino acid derived from a CDR2 region of a heavy chain or a light chain of the monoclonal antibody.

(2) In the method described in the above aspect (1), the monoclonal antibody is trastuzumab or trastuzumab-DM1, and a detection target is a peptide having an amino acid sequence expressed in SEQ ID No: 1, 3, 6 and/or 7.

(3) In the method described in the above aspect (2), the detection target is detected by multiple reaction monitoring under conditions described in Table 2 or 3.

(4) In the method described in the above aspect (1), the monoclonal antibody is bevacizumab, and a detection target is a peptide having an amino acid sequence expressed in SEQ ID No: 9-11.

(5) In the method described in the above aspect (4), the detection target is detected by multiple reaction monitoring under conditions described in Table 4.

(6) In the method described in the above aspect (1), the monoclonal antibody is rituximab, and a detection target is a peptide having an amino acid sequence expressed in SEQ ID No: 13, 15 and/or 16.

(7) In the method described in the above aspect (6), the detection target is detected by multiple reaction monitoring under conditions described in Table 5.

The present specification incorporates a disclosure content of Japanese Patent Application No. 2015-046059 on which priority of the present application is based.

Effect of the Invention

Since the method of the present invention is a limiting protease reaction field, it is possible to selectively decompose and collect a variable region of an antibody, in particular, a CDR2 region. The CDR2 region is an exposed part closest to a surface of the antibody and thus is preferentially decomposed. Utilizing this fact, detection of a monoclonal antibody using mass spectrometry can be more efficiently performed. Since the CDR2 region of an antibody drug can be selectively collected, by quantifying a peptide containing that region, concentration of the antibody drug can be directly measured from a biological sample.

BRIEF DESCRIPTION OF THE DRAWINGS

FIG. 6 illustrates calibration curves for quantitative analyses of bevacizumab CDR peptides added in plasma: (A) FTFSLDTSK (SEQ ID No: 10) and (B) VLIYFTSSLHS-GVPSR (SEQ ID No: 11).

MODE FOR CARRYING OUT THE INVENTION

Figure 1:
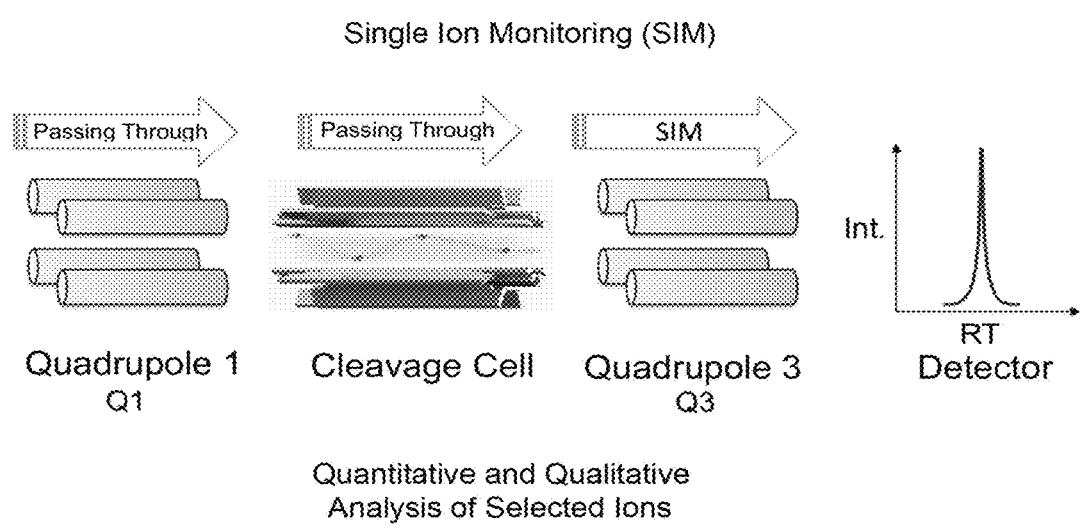
FIG. 1 schematically illustrates an analysis method based on single ion monitoring (SIM).

The present invention relates to a method in which a porous body in which a monoclonal antibody to be measured is immobilized in pores and nanoparticles on which a protease is immobilized are brought into contact with each other in a liquid to perform selective proteolysis of the monoclonal antibody; a resulting peptide fragment is detected using liquid chromatography-mass spectrometry (LC-MS); the porous body has an average pore diameter in a range of 10 nm-200 nm; the nanoparticles have an average particle size in a range of 50 nm-500 nm; the average particle size of the nanoparticles is larger than the average pore diameter of the porous body; and a peptide fragment to be detected has an amino acid sequence that includes an amino acid derived from a CDR2 region of a heavy chain or a light chain of the monoclonal antibody.

A "CDR region" is a term expressing a region where amino acid substitution particularly frequently occurs in an antibody, and is defined by a DNA editing location (exon and intron structure). In the method of the present invention, a peptide to be quantified as a detection target is selected with the CDR region as an indicator by looking at regions in vicinities of front and back of the CDR region; after a sequence alignment analysis, a peptide with specificity is used; and further, whether or not there is crossing with an endogenous antibody in blood can be verified based on a measured value.

In the present specification, the term "CDR2 (region)" refers to a region that includes, in addition to a region defined as a CDR2 by specific consecutive amino acid residues in a primary structure of an antibody, a region that defines specificity of the antibody as a whole in close proximity to the region defined as the CDR2 in a three-dimensional structure of the antibody. Further, in the present specification, similar to the above, references to "CDR1 (region)" and "CDR3 (region)" also each include a region that defines specificity of an antibody in a three-dimensional structure of the antibody. It is known that, even in a region commonly referred to as a framework region (FR), there is a difference in a sequence depending on an antibody. A sequence of an FR region may also depend on an origin of an antibody protein, a production process, and the like. A person skilled in the art can determine an amino acid sequence containing an amino acid derived from a CDR2 region for efficiently detecting specificity of a target antibody, and select a peptide fragment to be detected, by confirming multiple alignments of an amino acid sequence between a target antibody and another antibody and cross reactivity between the target antibody and an endogenous antibody.

Further, in the present specification, the term "amino acid sequence containing an amino acid derived from a CDR2 region" means an amino acid sequence containing at least one amino acid derived from a CDR2 region specific to a target antibody. In an analysis using mass spectrometry, when there is at least one amino acid residue defining specificity, the specificity can be reliably detected. The term "amino acid sequence containing an amino acid derived from a CDR2 region" is not intended to mean an arbitrary amino acid sequence containing "an amino acid derived from a CDR2 region," but is intended to mean that the amino acid sequence as a whole forms a continuous sequence of a portion of an amino acid sequence of a target antibody.

In the following, the method of the present invention is described in detail.

<Outline of Mass Spectrometry>

In recent years, a quantification technique using mass spectrometry is mainly performed using a hybrid mass spectrometer called a triple quadrupole. Specifically, an ionized biomolecule first passes through a portion called an octopole, thereby reducing an ion molecular vibration radius thereof. Next, in a first quadrupole, an ion having a specific mass number is selected by causing the ion to resonate, and other ions are excluded. This step is also referred to as single ion monitoring (SIM) (FIG. 1).

Figure 2:
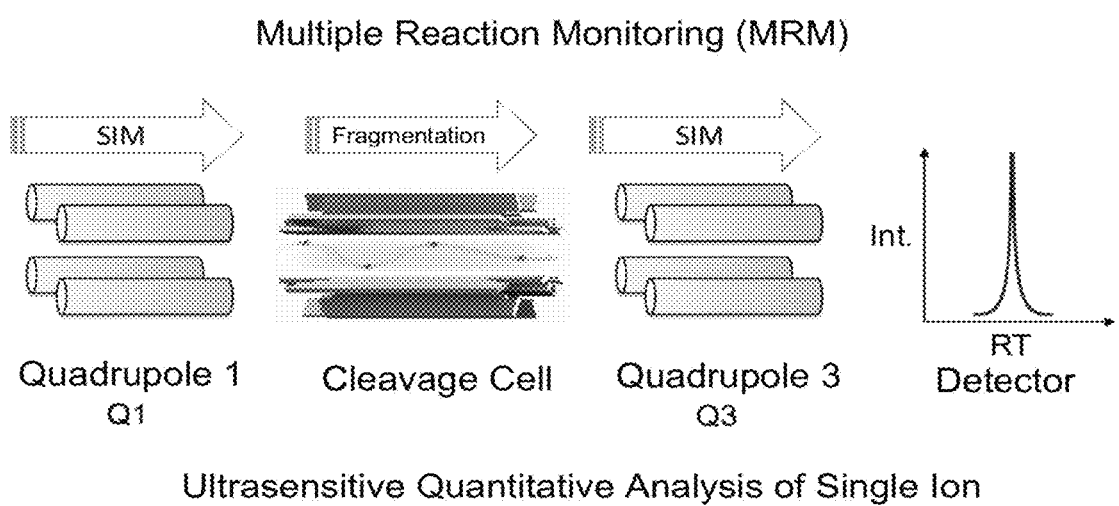
FIG. 2 schematically illustrates an analysis method based on multiple reaction monitoring (MRM).

The selected ion is brought to a second quadrupole, and cleavage is performed by colliding with argon. This reaction is referred to as collision-induced dissociation (CID). As a result of this cleavage reaction, a generated specific fragment is selected at a third quadrupole, and thereby, highly sensitive and highly selective quantification becomes possible. This series of analyses is referred to as multiple reaction monitoring (MRM) (FIG. 2).

Quantification of a biological sample using mass spectrometry has a greatest advantage that the quantification can be performed using a biomolecule structure-specific ion as an indicator, and, by connecting this to a high performance liquid chromatograph, continuous analysis can be performed. Among existing analytical instruments, this is a technology having an advantage that is substantially unique.

In order to detect an antibody using mass spectrometry, it is necessary to first extract the antibody from a biological sample such as blood or a tissue and to dissolve the antibody in an appropriate solvent. Further, since a molecule of an antibody is large for analysis, the antibody is decomposed into peptides by protease, and thereafter, mass spectrometry is performed after the peptides are separated using liquid chromatography. A molecular weight of a peptide suitable for analysis is about 1000-3000 Da.

However, when a common protein molecule is decomposed by protease, about 100 peptide fragments are generated, and in the case of an antibody, peptide fragments in a number far exceeding 200 are generated. Therefore, even for a single protein, the number of measurement targets becomes enormous, and when a complex biological sample is targeted, a huge sample set is involved.

Further, in an antibody molecule, only a small portion of a sequence such as a CDR region is different, and the remaining portion is a common sequence. Therefore, in order to analyze and quantify only a target specific sequence from the above huge and complex sample, liquid chromatography having high resolution and good reproducibility is necessary before a mass spectrometry step. Currently, there is a super high speed and high pressure chromatography instrument, and, corresponding to this instrument, a very fine column resin or the like having a uniform particle size has been developed. By using such a high speed, highly separable and high pressure resistant column, it is possible to dramatically improve resolution capability. However, it is still insufficient in research fields such as proteomics targeting protein sets.

Figure 3:
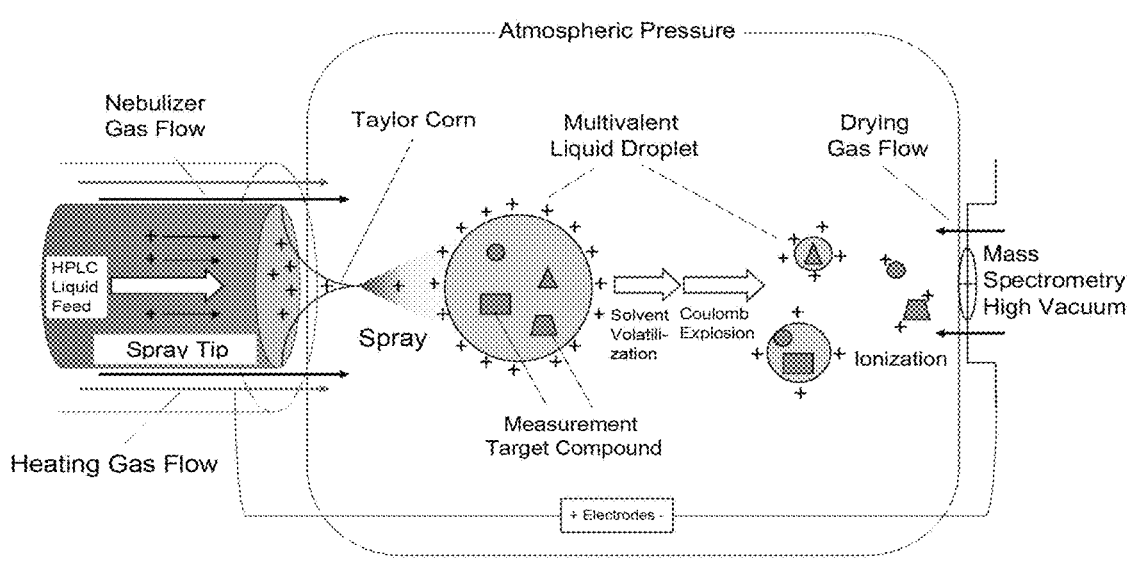
FIG. 3 illustrates a principle of an electrospray ionization method.

Next, an outline of an electrospray ionization method is illustrated in FIG. 3. As a problem in analysis using high-accuracy mass spectrometry, there is a "matrix effect." The "matrix effect" is a phenomenon in which ionization efficiency of a target substance is decreased due to presence of an ionization inhibitor in the same droplet, or due to presence of various kinds of ions at the same time. Since energy supplied to ionization is equal, when the number of ionization target substances increases, the energy is inevitably dispersed and an amount of ions decreases.

When the number of peptides to be analyzed increases, it is difficult to completely separate the peptides by column separation. Therefore, a decrease in ionization efficiency due to the matrix effect results in a decrease in sensitivity and quantitative reproducibility. In order to improve this, improvements are attempted on the mass spectrometry side by creating a high-speed channel switching function and the like. However, fundamentally, unless population is reduced, this matrix effect cannot be overcome.

In consideration of the various problems as described above, the method of the present invention is intended to reduce population to be analyzed while maintaining specificity of a measurement target.

<Antibody>

Figure 4:
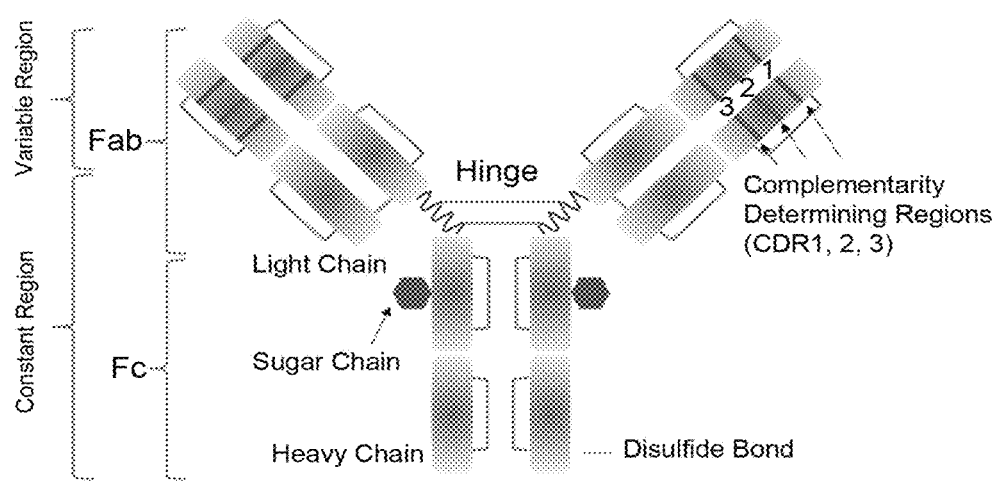
FIG. 4 illustrates a schematic diagram of an antibody.

A measurement target in the method of the present invention is a monoclonal antibody. A monoclonal antibody is an immunoglobulin (IgG) and, as illustrated in FIG. 4, is a biopolymer having a structure in which two heavy chains (each having a molecular weight of 50 kDa) and two light chains (each having a molecular weight of 25 kDa) are connected by a disulfide bond. An Fab domain and an Fc domain are connected via a hinge, and the heavy chains and light chains are respectively formed of a constant region and a variable region. The constant region has a structure (framework structure) that maintains a characteristic Y shape of an antibody, and has an amino acid sequence that is common to most of antibodies derived from the same specie. On the other hand, each variable region has three sites each having a specific sequence called a complementarity determining region (CDR). A three-dimensional structure defined by the CDR (CDR1, CDR2, CDR3) regions is involved in specific binding with an antigen, and thereby, an antibody-antigen complex is formed.

Further characteristics of a higher order structure of an antibody are very flexible hinge and variable region with respect to a constant region having a rigid structure. It is known that there is a site where a specific protein called Protein A or Protein G binds to a C terminus of a heavy chain.

In recent years, a large number of monoclonal antibodies have been developed as antibody drugs that can specifically act on various diseases. The method of the present invention is a very effective method for detecting such monoclonal antibodies. A monoclonal antibody that can be a measurement target in the method of the present invention is not limited. However, examples of the monoclonal antibody include: human antibodies such as panitumumab, ofatumumab, golimumab, and ipilimumab; humanized antibodies such as tocilizumab, trastuzumab, trastuzumab-DM1, bevacizumab, omalizumab, mepolizumab, gemtuzumab, palivizumab, ranibizumab, certolizumab, ocrelizumab, mogamulizumab, and eculizumab; chimeric antibodies such as rituximab, cetuximab, infliximab, and basiliximab; and the like. A monoclonal antibody has a molecular diameter of about 14.5 nm.

Further, a complex having an additional function while maintaining specificity of a monoclonal antibody, such as an Fc fusion protein, an antibody-drug complex (such as gemtuzumab-ozogamicin, trastuzumab-emtansin, or the like), is also included in monoclonal antibodies to be measured in the method of the present invention. In this case, it is possible that the binding of a complex is dissociated prior to measurement, and only an antibody is subjected to LC-MS, or it is also possible that a complex is subjected to LC-MS. A person skilled in the art can set an optimal condition for the method of the present invention according to a measurement target based on the description of this specification.

According to the method of the present invention, especially a CDR2 region of a monoclonal antibody can be regioselectively protease-digested, and identification and quantification of the antibody can be performed based on mass spectrometry of a resulting peptide fragment. The analysis method of the present invention is a method in which, by detecting a peptide fragment derived from a variable region of an antibody, especially a fragment of a CDR2 region, detection and quantification of the antibody is performed, and the peptide fragment derived from the antibody is directly measured. The analysis method of the present invention is applicable regardless of a kind of an antibody. Therefore, without being limited to the above exemplified antibodies, the method of the present invention is also applicable to newly developed monoclonal antibodies and the like.

<Porous Body>

A porous body ("antibody Fc immobilization resin" in FIG. 5) used in the method of the present invention is not particularly limited as long as the porous body has a large number of pores, and activated carbon, a porous membrane, porous resin beads, metal particles, and the like, can be used. Among these, those capable of site-specifically binding an antibody are particularly preferable.

Figure 5:
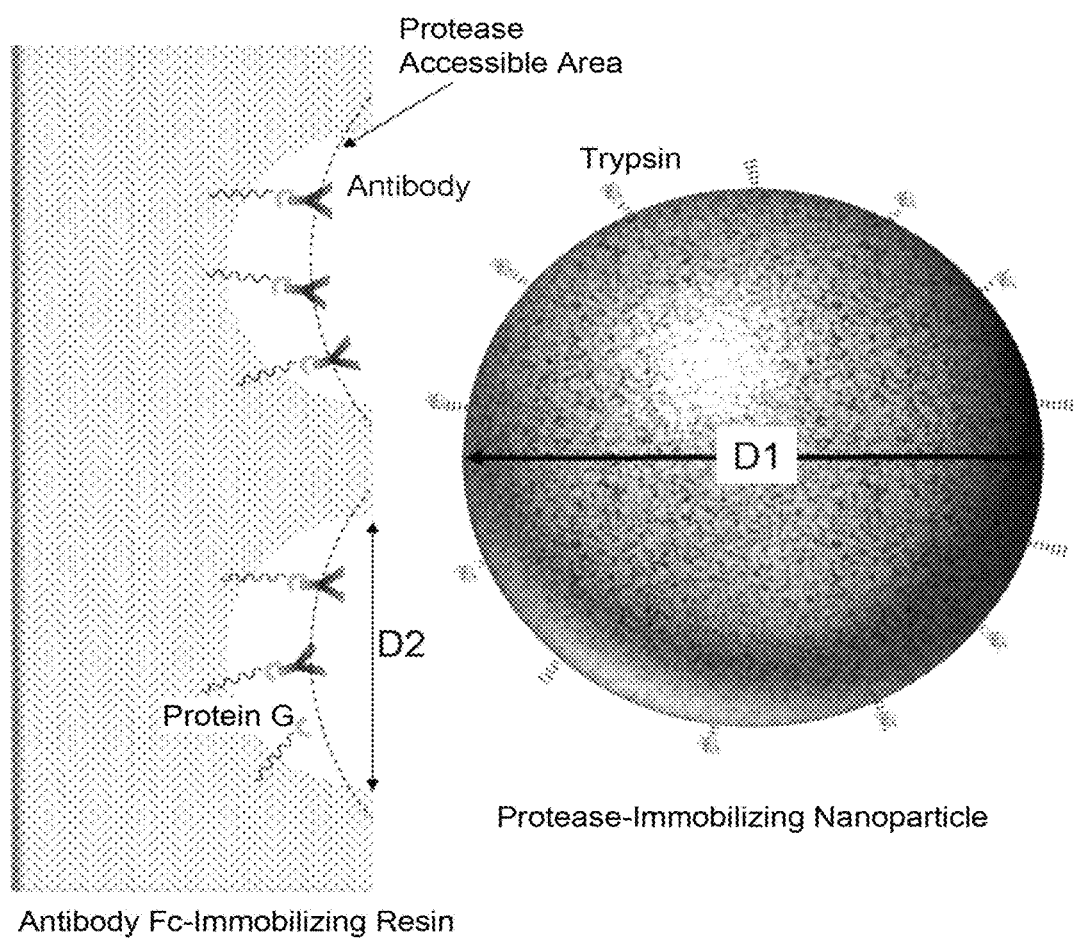
FIG. 5 illustrates a principle of a method of the present invention.

FIG. 5 illustrates hemispherical pores. However, the pores are not particularly limited in shape. Further, as in a case of a porous membrane, a porous body having pores formed penetrating the porous body can also be used. A size of a pore of a porous body is not particularly limited, and is preferably determined by considering a molecular diameter of an antibody and the like such that, when an antibody is immobilized, a part to be selectively digested is positioned near a surface layer of a pore. An average pore diameter (D2) of a porous body is appropriately set in a range of about 10 nm-200 nm and in a range smaller than an average particle size (D1) of nanoparticles. The average pore diameter (D2) of a porous body is, for example, preferably about 20 nm-200 nm, and more preferably about 30 nm-150 nm. In order to immobilize an Fc domain of an antibody in a pore and to regioselectively protease-digest an Fab domain, a pore diameter of a porous body is preferably 30 nm-150 nm, more preferably 40 nm-120 nm, even more preferably 50 nm-100 nm, and particularly preferably about 100 nm.

In the method of the present invention, a monoclonal antibody to be measured is immobilized in pores of a porous body. By immobilizing an antibody in pores and allowing the antibody to exist in a fine environment such as an interface between a solid phase and a liquid phase, the antibody is susceptible to denaturation, molecular fluctuation is subjected to perturbation, and probability of being attacked by a protease is increased. Further, in the present invention, as will be described later, by immobilizing a protease on nanoparticles, the protease is sterically stable and is in an environment in which autolysis is unlikely to occur, and thus, stability of the protease is increased. Therefore, according to the method of the present invention, in addition to allowing regioselective proteolysis, high protease activity can be maintained.

In the present invention, a porous body in which a linker molecule that site-specifically interacts with an antibody is immobilized in a pore of the porous body is preferably used. Examples of the interaction between the antibody and the linker molecule include chemical bonding, hydrogen bonding, ionic bonding, complex formation, a hydrophobic interaction, a van der Waals interaction, an electrostatic interaction, a stereoselective interaction, and the like.

As a linker molecule, Protein A, Protein G or the like that site-specifically binds with an Fc domain of an antibody is preferably used. By using a porous body in which these linker molecules are immobilized in pores, an Fc domain of an antibody is immobilized in a pore, and an Fab domain is positioned near a surface layer of the pore. In this way, by controlling orientation of an antibody in a pore, position selective digestion of an Fab domain by a protease becomes possible.

A size of a linker molecule is selected such that a selective cleavage site of an antibody is positioned near a surface layer of a pore. A molecular size in a state in which a linker molecule and an antibody are bound to each other is preferably about 0.5 times-1.5 times, more preferably about 0.6 times-1.2 times, even more preferably about 0.7 times-1.1 times, and particularly preferably about 0.8 times-1 times a pore diameter of a porous body. When a linker molecule is not fixed to a porous body and an antibody is directly bound in a pore, it is preferable that a molecular diameter of the antibody and a pore diameter of the porous body satisfy the above relation.

A porous body that can be suitably used in the present invention is not particularly limited. For example, Protein G Ultralink resin (manufactured by Pierce Corporation), Toyopearl, TSKgel (manufactured by (TOSOH Inc.), and the like can be used. For example, in the case of the Protein G Ultralink resin, it is known that 95% of Protein G bound to resin are in pores.

<Immobilization of Antibody in Porous Body>

A method for immobilizing an antibody in pores of a porous body is not particularly limited. An appropriate method can be adopted according to characteristics of the antibody, the porous body or a linker molecule and the like. For example, when an antibody is immobilized in a porous body in which a protein A or a protein G is immobilized in pores, by mixing a suspension of the porous body with a solution containing the antibody, the antibody can be easily immobilized in pores.

A quantitative ratio of a porous body to an antibody can be appropriately set according to a purpose. For example, when a quantitative analysis of an antibody is performed, it is desirable that almost the entire antibody in a sample be immobilized in the porous body. Therefore, it is preferable that a quantitative ratio be set such that an amount of the porous body becomes excessive with respect to an estimated content of the antibody in the sample.

<Nanoparticles>

In the method of the present invention, nanoparticles are used to immobilize a protease on surfaces of the nanoparticles and to control access of the protease to an immobilized antibody in pores of a porous body. Therefore, the nanoparticles have a larger average particle size (D1) than the average pore diameter (D2) of the porous body so as not to enter deep into the pores of the porous body (FIG. 5).

The nanoparticles are not particularly limited in shape. However, from a point of view of homogenization of access of the protease to the pores of the porous body, spherical nanoparticles are preferred. Further, it is preferable that the nanoparticles have high dispersibility and a uniform particle size.

The average particle size (D1) of the nanoparticles is in a range of 50 nm-500 nm, and is more preferably 1.2 or more times, even more preferably 1.5 or more times, and particularly preferably 1.8 or more times, for example, about 2 times the average pore diameter (D 2) of the porous body. For example, when the average pore diameter of the porous body is about 30-150 nm, the average particle size (D1) of the nanoparticles is preferably 100 nm or more, and more preferably 150 nm or more. When the average pore diameter of the porous body is about 50 nm-100 nm, the average particle size of the nanoparticles is preferably 120 nm or more, more preferably 150 nm or more, and particularly preferably 170 nm or more. From a point of view of improving proteolysis efficiency by the protease, an upper limit of the average particle size (D1) of the nanoparticles is preferably 500 nm or less, and more preferably 300 nm or less.

A material of the nanoparticles is not particularly limited as long as the above protease can be immobilized on surfaces of the nanoparticles. A metal, a resin, or the like can be appropriately used as the material of the nanoparticles. Further, a metal coated with a resin, a resin coated with a metal, or the like can also be used.

As a kind of the nanoparticles, magnetic nanoparticles that can be dispersed or suspended in an aqueous medium and can be easily recovered from the dispersion or suspension by magnetic separation or magnetic precipitation separation are preferable. Further, from a point of view that aggregation is less likely to occur, magnetic nanoparticles covered with an organic polymer are more preferable. Examples of base materials of magnetic nanoparticles include ferromagnetic alloys such as iron oxide (magnetite ($Fe_3O_4$), maghemite ($\gamma$-$Fe_2O_3$)), and ferrite ($Fe/M)_3O_4$. In the ferrite ($Fe/M)_3O_4$, M means a metal ion that can be used together with an iron ion to form a magnetic metal oxide, and typically, $Co^{2+}$, $Ni^{2+}$, $Mn^{2+}$, $Mg^{2+}$, $Cu^{2+}$, $Ni^{2+}$ and the like are used. Further, examples of the organic polymer covering the magnetic nanoparticles include polyglycidyl methacrylate (poly GMA), a copolymer of GMA and styrene, polymethyl methacrylate (PMMA), polymethyl acrylate) (PMA), and the like. Specific examples of magnetic nanobeads coated with an organic polymer include FG beads, SG beads, Adembeads, nanomag, and the like. As a commercially available product, for example, FG beads (polymer magnetic nanoparticles having a particle size of about 200 nm obtained by coating ferrite particles with polyglycidyl methacrylate (poly GMA)) manufactured by Tamagawa Seiki Co., Ltd. is suitably used.

In order to suppress adsorption of a nonspecific protein and to selectively immobilize a protease, it is preferable that the nanoparticles be modified with spacer molecules capable of binding to the protease. By immobilizing a protease via a spacer molecule, desorption of the protease from surfaces of nanoparticles is suppressed, and position selectivity of proteolysis is improved. Further, by adjusting a molecular size of a spacer, a protease can be caused to selectively access a desired position of an antibody, and position selectivity can be improved.

A spacer preferably can bind to protease and does not inactivate a protease. From a point of view of controlling an access range of a protease immobilized on surfaces of nanoparticles, a spacer preferably has a small molecular diameter. The molecular diameter of the spacer is preferably 5 nm or less, more preferably 3 nm or less, and even more preferably 2 nm or less. Further, a molecular weight of the spacer is preferably 2000 or less, more preferably 1500 or less, and even more preferably 1000 or less.

A spacer molecule having the above molecular diameter and capable of immobilizing a protease is preferably a non-protein, and is preferably a molecule having a functional group at a terminal, examples of the functional group including an amino group, a carboxyl group, an ester group, an epoxy group, a tosyl group, a hydroxyl group, a thiol group, an aldehyde group, a maleimide group, a succinimide group, an azide group, a biotin, an avidin, and a chelate. For example, for immobilization of trypsin, a spacer molecule having an activated ester group is preferred. Further, of a spacer molecule, as a spacer arm portion other the functional group, a hydrophilic molecule can be used, examples of the hydrophilic molecule including polyethylene glycol and its derivatives, polypropylene glycol and its derivatives, polyacrylamide and its derivatives, polyethyleneimine and its derivatives, poly (ethylene oxide) and its derivatives, poly (ethylene terephthalic acid) and its derivatives, and the like.

Nanoparticles surface-modified with such spacer molecules are also commercially available, and these nanoparticles can be used. For example, nanoparticles modified with a spacer molecule having an ester group (active ester group) activated with N-hydroxysuccinimide is commercially available under a trade name "FG beads NHS" (Tamagawa Seiki Co., Ltd.). The FG beads NHS has a particle size of about 200 nm±20 nm, and is very homogeneous as nanoparticles.

<Protease>

In the method of the present invention, a protease cleaves an antibody immobilized in pores of a porous body at a specific amino acid sequence site to generate a peptide fragment containing an amino acid of a CDR2 region.

In the present invention, a kind of a protease to be immobilized on nanoparticles may be appropriately selected according to a kind of a protein to be quantified or identified using mass spectrometry, and is not limited. Examples of the protease include trypsin, chymotrypsin, lysyl endopeptidase, V8 protease, Asp N protease (Asp-N), Arg C protease (Arg-C), papain, pepsin, dipeptidyl peptidase, and the like. Two or more kinds of these proteases can be used in combination.

Among the above proteases, trypsin is particularly preferably used in the present invention. Trypsin has high substrate specificity and has Lys or Arg at a C terminus of a peptide after cleavage and thus can homogenize a charge amount and charge localization of a peptide, and is particularly suitable for preparation of samples for mass spectrometry. Further, trypsin has a small molecular diameter (about 3.8 nm) and an active site exists inside a molecule. Therefore, a region where the active site can access an antibody is restricted, and position selectivity of proteolysis can be improved.

When a peptide fragment of an antibody after proteolysis is subjected to mass spectrometry as a measurement material, it is preferable to use a protease having less autolysis and high cleavage sequence selectivity. When a commercially available protease is used, it is preferable to use a protease of a mass spectrometry grade or a sequencing (sequence) grade. For example, native trypsin derived from a living body generates pseudo trypsin showing chymotrypsin-like activity by autolysis and thus is known to have low cleavage site specificity. Therefore, trypsin of a mass spectrometry grade having improved resistance to autolysis by subjecting lysine residue of the trypsin to reductive methylation is commercially available.

Examples of the protease that can be suitably used in the method of the present invention include Trypsin Gold (manufactured by Promega), Trypsin TPCK-Treated (manufactured by Sigma), and the like.

<<Immobilization of Protease on Nanoparticles>>

A method for immobilizing a protease on surfaces of nanoparticles is not particularly limited. An appropriate method can be adopted according to characteristics of the protease and the nanoparticles (or spacer molecules modifying the surfaces of the nanoparticles). For example, when the protease is immobilized on spacer-modified surfaces of the nanoparticle, by mixing a suspension of the nanoparticles and a solution containing the protease, the protease can be immobilized on the surfaces of the nanoparticles. An amine coupling method of the nanoparticles and the protease via the functional groups of the spacer molecules is preferable. For example, a carboxyl group surface-modified on nanoparticles can be esterified with N-hydroxysuccinimide (NHS) to form an activated ester group to which an amino group of a protease can be bound. This coupling reaction can be performed in the presence of carbodiimide as a condensing agent, examples of the carbodiimide including 1-ethyl-3-(3-dimethylaminopropyl) carbodiimide (EDAC), N,N'-dicyclohexylcarbodiimide (DCC), bis(2,6-diisopropylphenyl) carbodiimide (DIPC), and the like. Further, an amino group of a protease may be bound to an amino group surface-modified on nanoparticles using a cross-linking agent such as glutaraldehyde, bifunctional succinimide, bis(sulfosuccinimidyl) suberate (BS3), sulfonyl chloride, maleimide, and pyridyl disulfide.

The coupling method of the nanoparticles and the protease via the functional groups of the spacer molecules can be performed by a simple operation of adding a protease solution to a suspension of the nanoparticles and mixing and stirring the mixture under certain conditions.

After the protease is immobilized on the surfaces of the nanoparticles, it is preferable to inactivate an active portion that is not bound to the protease on the surfaces of the nanoparticles. For example, when spacer molecules on which the protease is not immobilized exist on the surfaces of the nanoparticles, problems may occur such as that the unbound spacer molecules bind to contaminants in the sample and adversely affects proteolysis, and that peptide fragments produced by proteolysis are immobilized on the nanoparticles. After the protease is immobilized, by blocking unbound spacer molecules, such problems are suppressed. As a method for inactivating the active portion unbound to the protease, chemical modification is preferred. For example, an activated ester group can be inactivated by reacting with a primary amine to form an amide bond.

<Proteolysis>

By bringing the porous body in which the antibody is immobilized and the nanoparticles on the surfaces of which the protease is immobilized into contact with each other in a liquid, the antibody is protease-digested and peptide fragments are produced. Here, the term "liquid" means that a substrate (solid phase) and an enzyme (solid phase) are in contact with each other in a liquid phase, and is intended to mean an aqueous medium suitable for a proteolysis reaction.

Conditions of proteolysis in the present invention are not particularly limited, and conditions similar to general proteolysis can be suitably adopted. For example, it is preferable to incubate at a temperature of about 37° C. for about 1 hour-20 hours in a buffer solution adjusted to a vicinity of an optimum pH of the protease.

A quantitative mixing ratio of the porous body on which the antibody is immobilized to the nanoparticles on the surfaces of which the protease is immobilized is not particularly limited, and may be set so as to have an amount of the protease corresponding to an amount of the antibody. A general proteolysis condition is that the ratio (substrate): (protease) is about 100:1-20:1 (weight ratio). In contrast, in the present invention, by a combination of the porous body and the nanoparticles, access between the antibody and the protease is physically restricted. Therefore, as compared to general proteolysis, it is preferable to increase the amount of the protease. For example, antibody:protease is preferably about 30:1-3:1, more preferably about 15:1-4:1, and even more preferably about 10:1-5:1.

In the method of the present invention, proteolysis is performed in a state in which the antibody is immobilized on the porous body. Since the peptide fragments produced by the proteolysis exist in the liquid phase, target peptide fragments can be regioselectively obtained without performing an antibody elution or denaturation operation. According to the method of the present invention, it is possible to regioselectively collect peptide fragments with a simple operation as compared to a conventional method.

More specifically, for example, a C-terminal side of an antibody is immobilized on a Protein G resin having a pore diameter of 100 nm, and a variable region of the antibody is always oriented to a solution side. Next, a protease is immobilized on surfaces of nanoparticles having a particle size of 200 nm. By limiting contact of a protease with the antibody, it is possible to form a reaction field in which a variable region selective antibody decomposition reaction is performed. Further, by using a surface of a nanoparticle having a very large relative surface area as a protease reaction field, probability of contact with an antigen can be increased.

The proteolysis is not particularly limited, and can be performed under tapping rotation accompanied by periodic tapping with stirring by gentle rotation. The term "gentle rotation" refers to, for example, a rotation speed of about 3-10 rpm, and the term "tapping" refers to a momentary action (frequency: for example, 1-5 times, preferably 2-4 times, per minute) such as flipping or imparting a shock. As a result, the porous body in which the antibody is immobilized and the nanoparticles on which the protease is immobilized are effectively brought into contact with each other while maintaining a dispersed state, and proteolysis reaction efficiency can be increased.

As described above, according to the method of the present invention, by limiting the contact between the monoclonal antibody, which is the substrate, and the protease, a peptide having an amino acid sequence containing an amino acid derived from a CDR2 region showing specificity of the monoclonal antibody can be efficiently digested and subjected to mass spectrometry.

<Removal of Porous Body and Nanoparticles>

In order to subject a target peptide fragment obtained by the proteolysis to mass spectrometry, it is necessary to remove the porous body and the nanoparticles. This can be achieved by subjecting a sample after the proteolysis to filtration, centrifugation, magnetic separation, dialysis, and the like.

When the porous body and the nanoparticles are removed by filtration, a pore diameter of a filtration membrane to be used is selected within a range that does not allow the porous body and the nanoparticles to pass and allows the digested peptide to pass. For example, by filtration using a filtration membrane made of polyvinylidene fluoride (PVDF) (low-binding hydrophilic PVDF having a hole diameter of 0.2 μm manufactured by Millipore Corporation), a filtration membrane made of polytetrafluoroethylene (PTFE) (low-binding hydrophilic PTFE having a hole diameter of 0.2 μm manufactured by Millipore Corporation), and the like, the porous body and the nanoparticles can be easily removed. When centrifugal filtration is adopted, filtration can be quickly and easily performed.

<Liquid Chromatography-Mass Spectrometry (LC-MS)>

By analyzing a sample containing the above-obtained peptide fragment using LC-MS, identification and quantification of the antibody can be performed.

For purposes such as more reliably separating the peptide fragment and improving analysis accuracy, a sample before being subjected to mass spectrometry is subjected to separation and concentration using liquid chromatography (LC). When separation of a sample is performed using LC, an eluate from LC may be directly ionized and subjected to mass spectrometry. Analysis can also be performed using LC/MS/MS or LC/MSn combining LC with tandem mass spectrometry. Further, the eluate from the LC may be collected once and then subjected to mass spectrometry. An LC column is not particularly limited, and a hydrophobic column such as C30, C18, C8, and C4 generally used in peptide analysis, a carrier for hydrophilic affinity chromatography, and the like can be appropriately selected and used.

Mass spectrometry can determine an amino acid sequence and thus can determine whether or not a peptide fragment is a peptide fragment derived from a specific protein such as an antibody. Further, based on a peak intensity, concentration of peptide fragments in a sample can be determined. In the present invention, since an antibody is subjected to regioselectively protease treatment, the number of types of peptide fragments contained in a sample is reduced. Therefore, conditions of analysis using mass spectrometry or the like can be easily set. In performing analysis, a sample may be used for the analysis after being subjected to treatments such as desalting, solubilization, extraction, concentration, and drying when necessary.

An ionization method in mass spectrometry is not particularly limited, and an electron ionization (EI) method, a chemical ionization (CI) method, a field desorption (FD) method, a fast atom collision (FAB) method, a matrix assisted laser desorption ionization (MALDI) method, an electrospray ionization (ESI) method, and the like can be adopted. A method for analyzing an ionized sample is also not particularly limited, and a method of a magnetic field deflection type, a quadrupole (Q) type, an ion trap (IT) type, a time of flight (TOF) type, a Fourier transform ion cyclotron resonance (FT-ICR) type, or the like can be appropriately determined according to the ionization method. Further, MS/MS analysis or multistage mass spectrometry of MS3 or higher can also be performed using triple quadrupole mass spectrometer or the like.

A device that is particularly suitable for being used in the method of the present invention is not particularly limited. Examples of the device include LCMS-8030, LCMS-8040, LCMS-8050, and LCMS-8080 (all manufactured by Shimadzu Corporation), and LCMS-IT-TOF and LCMS-Q-TOF (manufactured by Shimadzu Corporation).

Based on a mass spectrometry result, in order to identify an antibody, an existing database can also be used. In the present invention, a peptide fragment obtained by position-specifically protease-digesting an antibody is used. Therefore, a database search hit ratio and data accuracy are increased. Further, it is also possible to identify antibody by identifying an amino acid sequence of a peptide fragment using multistage mass spectrometry or the like. When a peptide fragment containing an amino acid sequence of a CDR2 region specific to an antibody can be detected, a target antibody can be identified and quantified.

When identification and quantification of an antibody are performed based on a detection result, the number of amino acid residues of a peptide to be detected is preferably about 5-30, and more preferably about 7-25. When the number of amino acid residues is excessively small, It is difficult to distinguish between contaminants and peptide fragments derived from other sites of the same protein, and this can cause erroneous detection. Further, when the number of amino acid residues is excessively large, for reasons such as that ionization becomes difficult, detection may become difficult and quantitativeness may decrease.

When concentration of an antibody is quantified, an amount of the antibody can be calculated based on a peak area or a peak intensity of a detected peptide fragment ion (in the case of multistage MS, a fragment ion obtained by cleavage of a parent ion). For example, based on a correlation between a predetermined calibration curve and a peak area, or a correlation between a peak area derived from an internal standard added to a sample and a peak area derived from the sample, concentration of peptide fragments in the sample is calculated, and, based on the concentration of the peptide fragments, an amount and concentration of the antibody are calculated.

A peptide fragment detected using mass spectrometry has an amino acid sequence containing an amino acid derived from a CDR 2 region of a monoclonal antibody to be measured. The detection may be performed using one kind of peptide or two or more kinds of peptides. Further, the method of the present invention does not exclude detection of a peptide having an amino acid sequence derived from a region other than a CDR2 region, and may also detect a peptide having an amino acid sequence containing an amino acid derived from a CDR1 region, a CDR3 region or the like, together with a peptide having an amino acid sequence derived from a CDR2 region.

Further, in mass spectrometry, it is well known that several kinds of fragment ions are generated in detection of one kind of peptide. By referring to results of analysis of internal standard peptides and results of analysis that are known in advance, it is possible to identify a target monoclonal antibody by detecting only one kind of ion of one kind of peptide. However, by simultaneously detecting and quantifying multiple fragment ions, for example, two or more kinds, three or more kinds, and four or more kinds of fragment ions, generated from one parent ion, more detailed structural information can be obtained. However, when an amount of fragment information is excessively large, an analysis time becomes longer, and, as a result, it leads to a decrease in analysis accuracy. Therefore, generally, with respect to one kind of parent ions, it is preferable to simultaneously monitor about 2-5 kinds of fragment ions. Further, for the fragment ions, as an ion series, it is desirable to select a y ion series. However, when the dominant candidate is not available, a b ion series may be selected next. Among the fragment ions, ions having a highest ion yield are used as ions for quantification and the other ions are used as ions for structure confirmation. Thereby, structure specificity can be ensured.

<Peptide Containing Amino Acid of CDR2 Region>

A peptide fragment to be detected in the method of the present invention has an amino acid sequence containing an amino acid derived from a CDR2 region of a heavy chain or a light chain of a monoclonal antibody of an antibody drug or the like. On a three-dimensional structure of an antibody, a CDR2 region exists on an outermost side and an upper side. Therefore, in limiting proteolysis in the method of the present invention, in terms of protease access, a peptide in this region can be detected with a highest efficiency.

Amino acid sequence information and the like of a monoclonal antibody intended to be used as an antibody drug are published, and information about amino acid sequences of a heavy chain and a light chain, Fab and Fc domains, CDR regions, a disulfide bond, and the like can be obtained. Examples of peptides obtained by trypsin-digesting trastuzumab, trastuzumab-DM1, bevacizumab, and rituximab using the method of the present invention are shown in Table 1.

TABLE 1

| Antibody | Peptide Sequence | SEQ ID No: | Chain | Region |
|---|---|---|---|---|
| Trastuzumab (or trastuzumab-DM1) | IYPTNGYTR | 1 | Heavy chain | CDR2 |
| Trastuzumab (or trastuzumab-DM1) | AEDTAVYYCSR | 2 | Heavy chain | CDR3 |
| Trastuzumab (or trastuzumab-DM1) | FTISADTSK | 3 | Heavy chain | CDR2 |
| Trastuzumab (or trastuzumab-DM1) | LSCAASGFNIK | 4 | Heavy chain | CDR1 |

TABLE 1-continued

| Antibody | Peptide Sequence | SEQ ID No: | Chain | Region |
|---|---|---|---|---|
| Trastuzumab (or trastuzumab-DM1) | DTYIHWVR | 5 | Heavy chain | CDR1 |
| Trastuzumab (or trastuzumab-DM1) | GLEWVAR | 6 | Heavy chain | CDR2 |
| Trastuzumab (or trastuzumab-DM1) | NTAYLQMNSLR | 7 | Heavy chain | CDR2 |
| Bevacizumab | AEDTAVYYCAK | 8 | Heavy chain | CDR3 |
| Bevacizumab | STAYLQMNSLR | 9 | Heavy chain | CDR2 |
| Bevacizumab | FTFSLDTSK | 10 | Heavy chain | CDR2 |
| Bevacizumab | VLIYFTSSLHSGVPSR | 11 | Light chain | CDR2 |
| Bevacizumab | LSCAASGYTFTNYGMNWVR | 12 | Heavy chain | CDR1 |
| Rituximab | ATLTADK | 13 | Heavy chain | CDR2 |
| Rituximab | VTMTCR | 14 | Light chain | CDR1 |
| Rituximab | LASGVPVR | 15 | Light chain | CDR2 |
| Rituximab | ATSNLASGVPVR | 16 | Light chain | CDR2 |
| Rituximab | FSGSGSGTSYSLTISR | 17 | Light chain | CDR3 |
| Rituximab | ASGYTFTSYNMHWVK | 18 | Heavy chain | CDR1 |
| Rituximab | ASSSVSYIHWFQQK | 19 | Light chain | CDR1 |

In Table 1, a peptide sequence containing an amino acid of a CDR2 region is shown in bold. In the method of the present invention, these peptide fragments each containing an amino acid of a CDR2 region are particularly suitable for identification and quantification of an antibody using mass spectrometry.

Therefore, when a monoclonal antibody to be measured is trastuzumab or trastuzumab-DM1, it is preferable to select a peptide having an amino acid sequence expressed in SEQ ID No: 1, 3, 6 and/or 7 as a detection target. In this case, for example, detection can be performed by multiple reaction monitoring using a triple quadrupole mass spectrometer (for example, LCMS-8050 manufactured by Shimadzu Corporation) with conditions described in Table 2 or 3 as indicators.

TABLE 2

Trastuzumab quantitation peptide and its mass spectrometry information

| Peptide Sequence | Parent ion mh | Fragment ion mh | Retention time [minutes] | Q1 Pre Bias [V] | Collision Energy [V] | Q3 Pre Bias [V] |
|---|---|---|---|---|---|---|
| IYPTNGYTR (SEQ ID NO. 1) | 542.8 | 808.4 | 3.405 | −40 | −18 | −30 |
| IYPTNGYTR (SEQ ID NO. 1) | 542.8 | 711.3 | 3.405 | −40 | −26 | −38 |
| IYPTNGYTR (SEQ ID NO. 1) | 542.8 | 610.3 | 3.405 | −40 | −24 | −22 |
| IYPTNGYTR (SEQ ID NO. 1) | 542.8 | 404.7 | 3.405 | −20 | −18 | −15 |
| IYPTNGYTR (SEQ ID NO. 1) | 542.8 | 277.2 | 3.405 | −20 | −16 | −30 |
| AEDTAVYYCSR (SEQ ID NO. 2) | 667.8 | 1134.5 | 3.473 | −24 | −24 | −34 |
| AEDTAVYYCSR (SEQ ID NO. 2) | 667.8 | 1019.5 | 3.473 | −24 | −25 | −30 |
| AEDTAVYYCSR (SEQ ID NO. 2) | 667.8 | 918.4 | 3.473 | −24 | −25 | −36 |
| AEDTAVYYCSR (SEQ ID NO. 2) | 667.8 | 847.4 | 3.473 | −24 | −23 | −32 |
| AEDTAVYYCSR (SEQ ID NO. 2) | 667.8 | 748.3 | 3.473 | −24 | −21 | −40 |
| AEDTAVYYCSR (SEQ ID NO. 2) | 667.8 | 585.2 | 3.473 | −24 | −24 | −22 |
| AEDTAVYYCSR (SEQ ID NO. 2) | 667.8 | 422.2 | 3.473 | −24 | −22 | −30 |
| AEDTAVYYCSR (SEQ ID NO. 2) | 667.8 | 488.2 | 3.473 | −24 | −20 | −25 |
| FTISADTSK (SEQ ID NO. 3) | 485.2 | 822.4 | 3.635 | −18 | −18 | −32 |
| FTISADTSK (SEQ ID NO. 3) | 485.2 | 721.4 | 3.635 | −11 | −18 | −26 |
| FTISADTSK (SEQ ID NO. 3) | 485.2 | 608.3 | 3.635 | −18 | −19 | −32 |
| FTISADTSK (SEQ ID NO. 3) | 485.2 | 521.3 | 3.635 | −18 | −19 | −38 |
| FTISADTSK (SEQ ID NO. 3) | 485.2 | 335.2 | 3.635 | −18 | −24 | −24 |
| LSCAASGFNIK (SEQ ID NO. 4) | 584.3 | 967.5 | 3.921 | −40 | −21 | −36 |
| LSCAASGFNIK (SEQ ID NO. 4) | 584.3 | 807.4 | 3.921 | −40 | −22 | −30 |
| LSCAASGFNIK (SEQ ID NO. 4) | 584.3 | 736.4 | 3.921 | −40 | −22 | −38 |
| LSCAASGFNIK (SEQ ID NO. 4) | 584.3 | 665.4 | 3.921 | −40 | −21 | −34 |
| LSCAASGFNIK (SEQ ID NO. 4) | 584.3 | 578.3 | 3.921 | −22 | −23 | −40 |
| LSCAASGFNIK (SEQ ID NO. 4) | 584.3 | 484.2 | 3.921 | −40 | −19 | −17 |

TABLE 2-continued

Trastuzumab quantitation peptide and its mass spectrometry information

| Peptide Sequence | Parent ion mh | Fragment ion mh | Retention time [minutes] | Q1 Pre Bias [V] | Collision Energy [V] | Q3 Pre Bias [V] |
|---|---|---|---|---|---|---|
| DTYIHWVR (SEQ ID NO. 5) | 363.9 | 597.3 | 4.097 | -27 | -17 | -22 |
| DTYIHWVR (SEQ ID NO. 5) | 363.9 | 460.3 | 4.097 | -27 | -19 | -23 |
| DTYIHWVR (SEQ ID NO. 5) | 363.9 | 437.2 | 4.097 | -27 | -11 | -30 |
| DTYIHWVR (SEQ ID NO. 5) | 363.9 | 299.2 | 4.097 | -26 | -16 | -21 |
| GLEWVAR (SEQ ID NO. 6) | 415.7 | 660.3 | 4.077 | -30 | -15 | -24 |
| GLEWVAR (SEQ ID NO. 6) | 415.7 | 531.3 | 4.077 | -30 | -16 | -40 |
| GLEWVAR (SEQ ID NO. 6) | 415.7 | 345.2 | 4.077 | -16 | -17 | -24 |
| GLEWVAR (SEQ ID NO. 6) | 415.7 | 246.2 | 4.077 | -30 | -18 | -17 |
| NTAYLQMNSLR (SEQ ID NO. 7) | 655.8 | 1095.6 | 4.144 | -24 | -23 | -42 |
| NTAYLQMNSLR (SEQ ID NO. 7) | 655.8 | 1024.5 | 4.144 | -24 | -22 | -40 |
| NTAYLQMNSLR (SEQ ID NO. 7) | 655.8 | 861.5 | 4.144 | -24 | -22 | -32 |
| NTAYLQMNSLR (SEQ ID NO. 7) | 655.8 | 748.4 | 4.144 | -24 | -23 | -28 |
| NTAYLQMNSLR (SEQ ID NO. 7) | 655.8 | 620.3 | 4.144 | -24 | -23 | -32 |
| NTAYLQMNSLR (SEQ ID NO. 7) | 655.8 | 489.3 | 4.144 | -24 | -23 | -25 |
| NTAYLQMNSLR (SEQ ID NO. 7) | 655.8 | 375.2 | 4.144 | -24 | -22 | -19 |

* Peptide containing C was subjected to a reductive alkylation treatment.

TABLE 3

Trastuzumab-DM1 quantitation peptide and its mass spectrometry information

| Peptide Sequence | Parent ion m/z | Fragment ion m/z | Retention time [minutes] | Q1 Pre Bias [V] | Collision Energy [V] | Q3 Pre Bias [V] |
|---|---|---|---|---|---|---|
| IYPTNGYTR (SEQ ID NO. 1) | 542.8 | 808.4 | 3.405 | -40 | -18 | -30 |
| IYPTNGYTR (SEQ ID NO. 1) | 542.8 | 711.3 | 3.405 | -40 | -26 | -38 |
| IYPTNGYTR (SEQ ID NO. 1) | 542.8 | 610.3 | 3.405 | -40 | -24 | -22 |
| IYPTNGYTR (SEQ ID NO. 1) | 542.8 | 404.7 | 3.405 | -20 | -18 | -15 |
| IYPTNGYTR (SEQ ID NO. 1) | 542.8 | 277.2 | 3.405 | -20 | -16 | -30 |
| AEDTAVYYCSR (SEQ ID NO. 2) | 667.8 | 1134.5 | 3.473 | -24 | -24 | -34 |
| AEDTAVYYCSR (SEQ ID NO. 2) | 667.8 | 1019.5 | 3.473 | -24 | -25 | -30 |
| AEDTAVYYCSR (SEQ ID NO. 2) | 667.8 | 918.4 | 3.473 | -24 | -25 | -36 |
| AEDTAVYYCSR (SEQ ID NO. 2) | 667.8 | 847.4 | 3.473 | -24 | -23 | -32 |
| AEDTAVYYCSR (SEQ ID NO. 2) | 667.8 | 748.3 | 3.473 | -24 | -21 | -40 |
| AEDTAVYYCSR (SEQ ID NO. 2) | 667.8 | 585.2 | 3.473 | -24 | -24 | -22 |
| AEDTAVYYCSR (SEQ ID NO. 2) | 667.8 | 422.2 | 3.473 | -24 | -22 | -30 |

TABLE 3-continued

Trastuzumab-DM1 quantitation peptide and its mass spectrometry information

| Peptide Sequence | Parent ion m/z | Fragment ion m/z | Retention time [minutes] | Q1 Pre Bias [V] | Collision Energy [V] | Q3 Pre Bias [V] |
|---|---|---|---|---|---|---|
| AEDTAVYYCSR (SEQ ID NO. 2) | 667.8 | 488.2 | 3.473 | −24 | −20 | −25 |
| FTISADTSK (SEQ ID NO. 3) | 485.2 | 822.4 | 3.635 | −18 | −18 | −32 |
| FTISADTSK (SEQ ID NO. 3) | 485.2 | 721.4 | 3.635 | −11 | −18 | −26 |
| FTISADTSK (SEQ ID NO. 3) | 485.2 | 608.3 | 3.635 | −18 | −19 | −32 |
| FTISADTSK (SEQ ID NO. 3) | 485.2 | 521.3 | 3.635 | −18 | −19 | −38 |
| FTISADTSK (SEQ ID NO. 3) | 485.2 | 335.2 | 3.635 | −18 | −24 | −24 |
| LSCAASGFNIK (SEQ ID NO. 4) | 584.3 | 967.5 | 3.921 | −40 | −21 | −36 |
| LSCAASGFNIK (SEQ ID NO. 4) | 584.3 | 807.4 | 3.921 | −40 | −22 | −30 |
| LSCAASGFNIK (SEQ ID NO. 4) | 584.3 | 736.4 | 3.921 | −40 | −22 | −38 |
| LSCAASGFNIK (SEQ ID NO. 4) | 584.3 | 665.4 | 3.921 | −40 | −21 | −34 |
| LSCAASGFNIK (SEQ ID NO. 4) | 584.3 | 578.3 | 3.921 | −22 | −23 | −40 |
| LSCAASGFNIK (SEQ ID NO. 4) | 584.3 | 484.2 | 3.921 | −40 | −19 | −17 |
| DTYLHWVR (SEQ ID NO. 5) | 363.9 | 597.3 | 4.097 | −27 | −17 | −22 |
| DTYLHWVR (SEQ ID NO. 5) | 363.9 | 460.3 | 4.097 | −27 | −19 | −23 |
| DTYLHWVR (SEQ ID NO. 5) | 363.9 | 437.2 | 4.097 | −27 | −11 | −30 |
| DTYLHWVR (SEQ ID NO. 5) | 363.9 | 299.2 | 4.097 | −26 | −16 | −21 |
| GLEWVAR (SEQ ID NO. 6) | 415.7 | 660.3 | 4.077 | −30 | −15 | −24 |
| GLEWVAR (SEQ ID NO. 6) | 415.7 | 531.3 | 4.077 | −30 | −16 | −40 |
| GLEWVAR (SEQ ID NO. 6) | 415.7 | 345.2 | 4.077 | −16 | −17 | −24 |
| GLEWVAR (SEQ ID NO. 6) | 415.7 | 246.2 | 4.077 | −30 | −18 | −17 |
| NTAYLQMNSLR (SEQ ID NO. 7) | 655.8 | 1095.6 | 4.144 | −24 | −23 | −42 |
| NTAYLQMNSLR (SEQ ID NO. 7) | 655.8 | 1024.5 | 4.144 | −24 | −22 | −40 |
| NTAYLQMNSLR (SEQ ID NO. 7) | 655.8 | 861.5 | 4.144 | −24 | −22 | −32 |
| NTAYLQMNSLR (SEQ ID NO. 7) | 655.8 | 748.4 | 4.144 | −24 | −23 | −28 |

TABLE 3-continued

Trastuzumab-DM1 quantitation peptide and its mass spectrometry information

| Peptide Sequence | Parent ion m/z | Fragment ion m/z | Retention time [minutes] | Q1 Pre Bias [V] | Collision Energy [V] | Q3 Pre Bias [V] |
|---|---|---|---|---|---|---|
| NTAYLQMNSLR (SEQ ID NO. 7) | 655.8 | 620.3 | 4.144 | −24 | −23 | −32 |
| NTAYLQMNSLR (SEQ ID NO. 7) | 655.8 | 489.3 | 4.144 | −24 | −23 | −25 |
| NTAYLQMNSLR (SEQ ID NO. 7) | 655.8 | 375.2 | 4.144 | −24 | −22 | −19 |

* Peptide containing C was subjected to a reductive alkylation treatment.

When a monoclonal antibody to be measured is bevacizumab, it is preferable to select a peptide having an amino acid sequence expressed in SEQ ID No: 9-11 as a detection target. In this case, for example, detection can be performed by multiple reaction monitoring using a triple quadrupole mass spectrometer (for example, LCMS-8050 manufactured by Shimadzu Corporation) with conditions described in Table 4 as indicators.

TABLE 4

Bevacizumab quantitation peptide and its mass spectrometry information

| Peptide Sequence | Parent ion m/z | Fragment ion m/z | Retention time [minutes] | Q1 Pre Bias [V] | Collision Energy [V] | Q3 Pre Bias [V] |
|---|---|---|---|---|---|---|
| AEDTAVYYCAK (SEQ ID NO. 8) | 645.8 | 1090.5 | 3.501 | −24 | −22 | −42 |
| AEDTAVYYCAK (SEQ ID NO. 8) | 645.8 | 975.5 | 3.501 | −24 | −24 | −38 |
| AEDTAVYYCAK (SEQ ID NO. 8) | 645.8 | 874.4 | 3.501 | −24 | −23 | −34 |
| AEDTAVYYCAK (SEQ ID NO. 8) | 645.8 | 803.4 | 3.501 | −24 | −20 | −30 |
| AEDTAVYYCAK (SEQ ID NO. 8) | 645.8 | 704.3 | 3.501 | −24 | −20 | −38 |
| AEDTAVYYCAK (SEQ ID NO. 8) | 645.8 | 541.2 | 3.501 | −24 | −21 | −40 |
| AEDTAVYYCAK (SEQ ID NO. 8) | 645.8 | 488.2 | 3.501 | −24 | −17 | −11 |
| AEDTAVYYCAK (SEQ ID NO. 8) | 645.8 | 587.3 | 3.501 | −24 | −17 | −22 |
| STAYLQMNSLR (SEQ ID NO. 9) | 642.3 | 1095.6 | 4.147 | −24 | −24 | −42 |
| STAYLQMNSLR (SEQ ID NO. 9) | 642.3 | 1024.5 | 4.147 | −24 | −25 | −40 |
| STAYLQMNSLR (SEQ ID NO. 9) | 642.3 | 861.5 | 4.147 | −24 | −25 | −20 |
| STAYLQMNSLR (SEQ ID NO. 9) | 642.3 | 748.4 | 4.147 | −24 | −22 | −28 |
| STAYLQMNSLR (SEQ ID NO. 9) | 642.3 | 620.3 | 4.147 | −24 | −24 | −32 |
| STAYLQMNSLR (SEQ ID NO. 9) | 642.3 | 489.3 | 4.147 | −24 | −22 | −25 |
| STAYLQMNSLR (SEQ ID NO. 9) | 642.3 | 375.2 | 4.147 | −24 | −22 | −27 |
| FTFSLDTSK (SEQ ID NO. 10) | 523.3 | 898.5 | 4.432 | −38 | −20 | −34 |
| FTFSLDTSK (SEQ ID NO. 10) | 523.3 | 797.4 | 4.432 | −38 | −18 | −30 |
| FTFSLDTSK (SEQ ID NO. 10) | 523.3 | 650.3 | 4.432 | −38 | −19 | −34 |
| FTFSLDTSK (SEQ ID NO. 10) | 523.3 | 563.3 | 4.432 | −38 | −22 | −40 |
| FTFSLDTSK (SEQ ID NO. 10) | 523.3 | 450.2 | 4.432 | −20 | −23 | −30 |
| FTFSLDTSK (SEQ ID NO. 10) | 523.3 | 335.2 | 4.432 | −20 | −25 | −24 |
| FTFSLDTSK (SEQ ID NO. 10) | 523.3 | 399.2 | 4.432 | −38 | −17 | −11 |
| FTFSLDTSK (SEQ ID NO. 10) | 523.3 | 249.1 | 4.432 | −38 | −17 | −17 |
| VLIYFTSSLHSGVPSR (SEQ ID NO. 11) | 588.3 | 832.4 | 4.515 | −22 | −19 | −30 |
| VLIYFTSSLHSGVPSR (SEQ ID NO. 11) | 588.3 | 775.9 | 4.515 | −22 | −18 | −28 |
| VLIYFTSSLHSGVPSR (SEQ ID NO. 11) | 588.3 | 719.4 | 4.515 | −22 | −18 | −26 |
| VLIYFTSSLHSGVPSR (SEQ ID NO. 11) | 588.3 | 637.8 | 4.515 | −22 | −18 | −24 |
| VLIYFTSSLHSGVPSR (SEQ ID NO. 11) | 588.3 | 564.3 | 4.515 | −22 | −22 | −20 |

TABLE 4-continued

Bevacizumab quantitation peptide and its mass spectrometry information

| Peptide Sequence | Parent ion m/z | Fragment ion m/z | Retention time [minutes] | Q1 Pre Bias [V] | Collision Energy [V] | Q3 Pre Bias [V] |
|---|---|---|---|---|---|---|
| VLIYFTSSLHSGVPSR (SEQ ID NO. 11) | 588.3 | 602.3 | 4.515 | -22 | -28 | -22 |
| VLIYFTSSLHSGVPSR (SEQ ID NO. 11) | 588.3 | 359.2 | 4.515 | -22 | -26 | -26 |
| VLIYFTSSLHSGVPSR (SEQ ID NO. 11) | 588.3 | 213.2 | 4.515 | -22 | -20 | -23 |
| LSCAASGYTFTNYGMNWVR (SEQ ID NO. 12) | 733.3 | 1039.5 | 4.896 | -28 | -25 | -40 |
| LSCAASGYTFTNYGMNWVR (SEQ ID NO. 12) | 733.3 | 848.4 | 4.896 | -28 | -18 | -32 |
| LSCAASGYTFTNYGMNWVR (SEQ ID NO. 12) | 733.3 | 925.4 | 4.896 | -28 | -25 | -36 |
| LSCAASGYTFTNYGMNWVR (SEQ ID NO. 12) | 733.3 | 762.4 | 4.896 | -28 | -26 | -40 |
| LSCAASGYTFTNYGMNWVR (SEQ ID NO. 12) | 733.3 | 705.4 | 4.896 | -26 | -24 | -34 |
| LSCAASGYTFTNYGMNWVR (SEQ ID NO. 12) | 733.3 | 574.3 | 4.896 | -28 | -22 | -30 |
| LSCAASGYTFTNYGMNWVR (SEQ ID NO. 12) | 733.3 | 520.2 | 4.896 | -28 | -18 | -36 |
| LSCAASGYTFTNYGMNWVR (SEQ ID NO. 12) | 733.3 | 503.2 | 4.896 | -28 | -18 | -36 |

\* Peptide containing C was subjected to a reductive alkylation treatment.

When a monoclonal antibody to be measured is rituximab, it is preferable to select a peptide having an amino acid sequence expressed in SEQ ID No: 13, 15 and/or 16 as a detection target. In this case, for example, detection can be performed by multiple reaction monitoring using a triple quadrupole mass spectrometer (for example, LCMS-8050 manufactured by Shimadzu Corporation) with conditions described in Table 5 as indicators.

TABLE 5

Rituximab quantitation peptide and its mass spectrometry information

| Peptide Sequence | Parent ion m/z | Fragment ion m/z | Retention time [minutes] | Q1 Pre Bias [V] | Collision Energy [V] | Q3 Pre Bias [V] |
|---|---|---|---|---|---|---|
| ATLTADK (SEQ ID NO.13) | 360.2 | 648.4 | 2.809 | -26 | -14 | -24 |
| ATLTADK (SEQ ID NO.13) | 360.2 | 547.3 | 2.81 | -13 | -13 | -20 |
| ATLTADK (SEQ ID NO.13) | 360.2 | 434.2 | 2.81 | -26 | -16 | -22 |
| ATLTADK (SEQ ID NO.13) | 360.2 | 333.2 | 2.81 | -26 | -19 | -24 |
| ATLTADK (SEQ ID NO.13) | 360.2 | 262.1 | 2.81 | -13 | -21 | -29 |
| VTMTCR (SEQ ID NO.14) | 384.2 | 668.3 | 2.887 | -28 | -16 | -34 |
| VTMTCR (SEQ ID NO.14) | 384.2 | 567.2 | 2.887 | -28 | -14 | -40 |
| VTMTCR (SEQ ID NO.14) | 384.2 | 436.2 | 2.887 | -28 | -16 | -16 |
| VTMTCR (SEQ ID NO.14) | 384.2 | 335.1 | 2.887 | -14 | -17 | -23 |
| VTMTCR (SEQ ID NO.14) | 384.2 | 201.1 | 2.887 | -28 | -14 | -21 |
| LASGVPVR (SEQ ID NO.15) | 399.7 | 685.4 | 3.426 | -29 | -17 | -34 |
| LASGVPVR (SEQ ID NO.15) | 399.7 | 614.4 | 3.426 | -30 | -16 | -32 |
| LASGVPVR (SEQ ID NO.15) | 399.7 | 527.3 | 3.426 | -15 | -16 | -38 |
| LASGVPVR (SEQ ID NO.15) | 399.7 | 371.2 | 3.426 | -15 | -17 | -28 |
| ATSNLASGVPVR (SEQ ID NO.16) | 586.3 | 912.5 | 3.728 | -22 | -25 | -34 |
| ATSNLASGVPVR (SEQ ID NO.16) | 586.3 | 685.4 | 3.728 | -22 | -23 | -38 |
| ATSNLASGVPVR (SEQ ID NO.16) | 586.3 | 614.4 | 3.728 | -22 | -25 | -24 |
| ATSNLASGVPVR (SEQ ID NO.16) | 586.3 | 527.3 | 3.728 | -22 | -25 | -40 |
| ATSNLASGVPVR (SEQ ID NO.16) | 586.3 | 470.3 | 3.728 | -22 | -19 | -17 |
| ATSNLASGVPVR (SEQ ID NO.16) | 586.3 | 371.2 | 3.728 | -22 | -17 | -27 |
| FSGSGSGTSYSLTISR (SEQ ID NO.17) | 803.9 | 1084.6 | 4.051 | -30 | -32 | -42 |
| FSGSGSGTSYSLTISR (SEQ ID NO.17) | 803.9 | 926.5 | 4.051 | -30 | -34 | -36 |
| FSGSGSGTSYSLTISR (SEQ ID NO.17) | 803.9 | 839.5 | 4.051 | -30 | -36 | -32 |
| FSGSGSGTSYSLTISR (SEQ ID NO.17) | 803.9 | 839.5 | 4.051 | -30 | -36 | -32 |

TABLE 5-continued

Rituximab quantitation peptide and its mass spectrometry information

| Peptide Sequence | Parent ion m/z | Fragment ion m/z | Retention time [minutes] | Q1 Pre Bias [V] | Collision Energy [V] | Q3 Pre Bias [V] |
|---|---|---|---|---|---|---|
| FSGSGSGTSYSLTISR (SEQ ID NO.17) | 803.9 | 589.4 | 4.051 | −30 | −34 | −22 |
| FSGSGSGTSYSLTISR (SEQ ID NO.17) | 803.9 | 476.3 | 4.051 | −30 | −32 | −17 |
| FSGSGSGTSYSLTISR (SEQ ID NO.17) | 803.9 | 375.2 | 4.051 | −30 | −33 | −27 |
| ASGYTFTSYNMHWVK (SEQ ID NO.18) | 597.9 | 1064.5 | 4.399 | −22 | −24 | −40 |
| ASGYTFTSYNMHWVK (SEQ ID NO.18) | 597.9 | 860.9 | 4.399 | −22 | −18 | −32 |
| ASGYTFTSYNMHWVK (SEQ ID NO.18) | 597.9 | 817.4 | 4.399 | −22 | −18 | −30 |
| ASGYTFTSYNMHWVK (SEQ ID NO.18) | 597.9 | 788.9 | 4.399 | −22 | −18 | −30 |
| ASGYTFTSYNMHWVK (SEQ ID NO.18) | 597.9 | 707.3 | 4.399 | −22 | −18 | −26 |
| ASGYTFTSYNMHWVK (SEQ ID NO.18) | 597.9 | 656.8 | 4.399 | −22 | −18 | −24 |
| ASGYTFTSYNMHWVK (SEQ ID NO.18) | 597.9 | 583.3 | 4.399 | −22 | −22 | −22 |
| ASSSVSYIHWFQQK (SEQ ID NO.19) | 556.6 | 798.9 | 4.399 | −20 | −17 | −30 |
| ASSSVSYIHWFQQK (SEQ ID NO.19) | 556.6 | 755.4 | 4.399 | −20 | −16 | −28 |
| ASSSVSYIHWFQQK (SEQ ID NO.19) | 556.6 | 711.9 | 4.399 | −20 | −19 | −26 |
| ASSSVSYIHWFQQK (SEQ ID NO.19) | 556.6 | 668.3 | 4.399 | −40 | −16 | −24 |
| ASSSVSYIHWFQQK (SEQ ID NO.19) | 556.6 | 618.8 | 4.399 | −20 | −17 | −22 |
| ASSSVSYIHWFQQK (SEQ ID NO.19) | 556.6 | 550.3 | 4.399 | −20 | −14 | −40 |
| ASSSVSYIHWFQQK (SEQ ID NO. 19) | 556.6 | 403.2 | 4.399 | −20 | −29 | −25 |

* Peptide containing C was subjected to a reductive alkylation treatment.

Examples

In the following, the present invention is described in detail based on Examples. However, the present invention is not limited by these Examples.

[Immobilization of Protease]

Protease was immobilized on nanoparticles by the following steps.

<1. FG Beads Cleaning>

200 mg of FG beads NHS (manufactured by Tamagawa Seiki Co., Ltd.) is subjected to centrifugal separation (15,000 g×5 minutes, 4° C.), and supernatant isopropanol for preservation is removed. Supernatant, including also floating substances that do not precipitated, is carefully removed.

<2. Preparation of Enzyme>

Five 1 mg Trypsin Golds (manufactured by Promega Corporation) are opened and are dissolved in 25 mM HEPES-NaOH at pH 7.0 cooled to 4° C. After the dissolution, the solution is put in a 50 ml centrifuge tube, which is then placed on ice. The enzyme is washed once with 25 mM HEPES-NaOH at pH 7.0 and is collected as much as possible. A final buffer volume is about 25 ml.

<3. FG Beads Cleaning>

10 ml of ice-cooled methanol is added, and, in an ice-cooled ultrasonic cleaning machine, a suspension of FG beads is confirmed and then is subjected to centrifugal separation (15,000 g×5 minutes, 4° C.), and supernatant methanol is removed.

<4. Enzyme Immobilization Reaction>

A trypsin solution. is added to 200 mg of a precipitate of FG beads. After a suspension of FG beads is confirmed using an ice-cooled ultrasonic washer, vortex is continuously performed for 30 minutes at a minimum speed that allows the suspension to be maintained. After allowing a reaction to proceed for 30 minutes, centrifugal separation (15,000 g×5 minutes, 4° C.) is performed, and supernatant is removed. The supernatant is collected and coupling efficiency due to BCA assay is confirmed.

<5. Active Group Block>

25 ml of 1M 2-aminoethanol hydrochloride at pH 8.0 is added to 200 mg of a precipitate of FG beads. After a suspension of FG beads is confirmed using an ice-cooled ultrasonic washing machine, vortex is continuously performed at a minimum speed that allows the suspension to be maintained. After blocking by allowing a reaction to proceed for 30 minutes, centrifugal separation is performed, and supernatant is removed.

<6. Enzyme Beads Cleaning>

25 ml of 25 mM HEPES-NaOH and 50 mM NaCl at pH 7.0 is added to 200 mg of a precipitate of FG beads. After a suspension of FG beads is confirmed using an ice-cooled ultrasonic washing machine, vortex is continuously performed at a minimum speed that allows the suspension to be maintained. After 5 minutes of washing, centrifugal separation is performed and supernatant is removed.

<7. Storage>

25 mM Tris-HCl at pH 8.0 is added such that a protease final concentration is 0.5 µg/µl. After a suspension of FG beads is confirmed using an ice-cooled ultrasonic washer, the solution is dispensed to 500 µl. Thereafter, the solution is stored at −80° C.

[Proteolysis]

A monoclonal antibody in a plasma sample was protease-digested by the following steps.

<1. Collection of Monoclonal Antibody from Plasma>

The monoclonal antibody is a family of immunoglobulin IgG and thus can be collected in the same way as immunoglobulins inherent in a plasma. 20 µl of a plasma is diluted with 180 µl of PBS+0.1% n-octyl-β-D-thioglucoside (manufactured by Dojin Chemical).

40 µl of a 50% suspension of Protein G Ultralink resin (manufactured by Pierce Corporation) is added. By slowly vortexing or rotating with a rotary mixer at a room temperature for 1-2 hours, antibody molecules in the plasma are bound to the resin. By centrifugal separation, the resin is precipitated and supernatant is discarded.

By adding 200 μl of PBS+0.1% n-octyl-β-D-thioglucoside and washing three times, proteins in the plasma non-specifically bound to the resin are washed. Next, by washing once with 200 μl of PBS, a surfactant is removed.

<2. Protease Reaction>

200 μl of 25 mM Tris-HCl at pH 8.0 is added to the tube in which the Protein G Ultralink resin remains. Next, 80 μl of nanoparticles on which trypsin is immobilized is added to the tube, which is set it in a rotator and is slowly rotated at 37° C. for 6 hours.

After reaction, by performing filtration with a 0.2 μm low binding hydrophilic PVDF membrane (manufactured by Millipore Corporation), the Protein G resin and the nanoparticles on which trypsin is immobilized are removed together, and a reaction solution is collected.

[Mass Spectrometry]

An antibody drug was spiked into a commercially available plasma (manufactured by Sigma Corporation) and its peptide was detected. As the monoclonal antibody, four kinds including trastuzumab (drug name: Herceptin, Chugai Pharmaceutical), trastuzumab-DM1 (drug name: CadSaila, Chugai Pharmaceutical), bevacizumab (drug name: Avastin, Roche Genetech), and rituximab (drug name: Rituxan, Chugai Pharmaceutical and Total Pharmaceutical Industry) were used. Conditions of mass spectrometry are as follows.

<HPLC Conditions (Nexera LC30A Liquid Chromatography System)>

Solvent A: 0.1% formic acid; solvent B: 0.1% formic acid+acetonitrile

Flow rate: 0.5 ml/minute

Gradient time: 1% B (1.5 minutes), 1-40% B gradient (5 minutes), 95% B (5 minutes), 1% B (5 minutes)

Column: L-column 2 ODS, 2×50 mm (Chemical Substance Evaluation and Research Organization)

Column temperature: 50° C.

<MS Interface Conditions (LCMS-8050 (Shimadzu Corporation))>

Nebulizer gas: 3 L/minute
Heating gas: 10 L/minute
Drying gas: 10 L/minute
Interface temperature: 300° C.
DL temperature: 250° C.
Heat block temperature: 400° C.

FIG. 6 illustrates an example in which bevacizumab is detected. FIG. 6 (A) shows results of performing mass spectrometry using a peptide FTFSLDTSK (SEQ ID No: 10) containing an amino acid of a CDR2 region of a heavy chain as a detection target peptide; and FIG. 6 (B) shows results of performing mass spectrometry using a peptide VLIYFTSSLHSGVPSR (SEQ ID No: 11) containing an amino acid of a CDR2 region of a light chain as a detection target peptide. Mass spectrometry information for these detections can be obtained by referring to the above Table 4.

As is clear from the results in FIG. 6, detection of the above peptide using mass spectrometry is highly accurate, and, when a calibration curve is produced from acquired data, in a range up to a bevacizumab concentration of 100 μg/ml, multiple correlation coefficient was $R^2=0.9999$ or $R^2=0.9998$.

[Comparison of Ionic Strength]

A peptide of an antibody drug protease-digested under the same conditions as above was detected using mass spectrometry. As the monoclonal antibody, three kinds including trastuzumab (drug name: Herceptin, Chugai Pharmaceutical), bevacizumab (drug name: Avastin, Roche Genetech), and rituximab (drug name: Rituxan, Chugai Pharmaceutical and Total Pharmaceutical Industry) were used.

The results are shown in Tables 6-8.

TABLE 6

| Antibody | Peptide Sequence | SEQ ID No: | Region | Ionic strength |
| --- | --- | --- | --- | --- |
| Trastuzumab | IYPTNGYTR | 1 | CDR2 | 208279 |
| Trastuzumab | AEDTAVYYCSR | 2 | CDR3 | ND |
| Trastuzumab | FTISADTSK | 3 | CDR2 | 98219 |
| Trastuzumab | LSCAASGFNIK | 4 | CDR1 | ND |
| Trastuzumab | DTYIHWVR | 5 | CDR1 | 4553 |
| Trastuzumab | GLEWVAR | 6 | CDR2 | 189915 |
| Trastuzumab | NTAYLQMNSLR | 7 | CDR2 | 86002 |

TABLE 7

| Antibody | Peptide Sequence | SEQ ID No: | Region | Ionic strength |
| --- | --- | --- | --- | --- |
| Bevacizumab | AEDTAVYYCAK | 8 | CDR3 | ND |
| Bevacizumab | STAYLQMNSLR | 9 | CDR2 | 276061 |
| Bevacizumab | FTFSLDTSK | 10 | CDR2 | 514838 |
| Bevacizumab | VLIYFTSSLHSGVPSR | 11 | CDR2 | 126726 |
| Bevacizumab | LSCAASGYTFTNYGMNWVR | 12 | CDR1 | ND |

TABLE 8

| Antibody | Peptide Sequence | SEQ ID No: | Region | Ionic strength |
| --- | --- | --- | --- | --- |
| Rituximab | ATLTADK | 13 | CDR2 | 220598 |
| Rituximab | VTMTCR | 14 | CDR1 | ND |
| Rituximab | LASGVPVR | 15 | CDR2 | 506239 |
| Rituximab | ATSNLASGVPVR | 16 | CDR2 | 16094 |
| Rituximab | FSGSGSGTSYSLTISR | 17 | CDR3 | 18961 |
| Rituximab | ASGYTFTSYNMHWVK | 18 | CDR1 | 45152 |
| Rituximab | ASSSVSYIEIWFQQK | 19 | CDR1 | 12287 |

As is clear from the results shown in Tables 6-8, using the method of the present invention, in all of trastuzumab, bevacizumab, and rituximab, a peptide fragment containing an amino acid derived from a CDR2 region could be detected with higher ionic strength than peptide fragments derived from other regions.

INDUSTRIAL APPLICABILITY

In the method of the present invention, in particular, a peptide containing an amino acid of a CDR2 region is selectively protease-digested and a resulting peptide fragment is subjected to mass spectrometry. Thereby, a sequence and an amount of the peptide fragment can be determined and an antibody can be identified and quantified. The method of the present invention is simple in operation and can ensure reproducibility and quantitativeness, and also allows automation to be achieved, and thus, can also be applied to analysis of pharmacokinetics, analysis of interaction using antigen antibody reaction, various interactome analyses, and basic researches such as identification of an immunoprecipitated protein. In addition, the method of the present invention is also expected to be applicable to sequence analysis of biomolecule drugs such as antibody drugs, quality assurance, identity confirmation of generic drugs, and the like.

Currently, 40 antibody drugs are on the market, and it is said that there are about 300 antibody drugs are in preclinical trials, more than 2,000 antibody drugs in all clinical trials including animal tests, and more than 5,000 antibody drugs when those in research stage and seeds are included. The present invention can provide an extremely versatile analysis method for such a wide variety of antibody drugs, and can contribute to acceleration of future antibody drug development.

All publications, patents and patent applications cited in the present specification are incorporated by reference in their entirety in the present specification.

What is claimed is:

1. A method of detecting a monoclonal antibody, comprising:
   bringing into contact in a liquid a porous body having pores in which a monoclonal antibody is immobilized and nanoparticles on which a protease is immobilized such that a selective proteolysis of the monoclonal antibody occurs; and
   detecting a peptide fragment by multiple reaction monitoring under conditions described below using liquid chromatography-mass spectrometry, Trastuzumab or trastuzumab-DM1 quantitation peptide and its mass spectrometry information

| Peptide Sequence | Parent ion m/z | Fragment ion m/z | Retention time [minutes] | Q1 Pre Bias [V] | Collision Energy [V] | Q3 Pre Bias [V] |
|---|---|---|---|---|---|---|
| IYPTNGYTR (SEQ ID NO. 1) | 542.8 | 808.4 | 3.405 | −40 | −18 | −30 |
| IYPTNGYTR (SEQ ID NO. 1) | 542.8 | 711.3 | 3.405 | −40 | −26 | −38 |
| IYPTNGYTR (SEQ ID NO. 1) | 542.8 | 610.3 | 3.405 | −40 | −24 | −22 |
| IYPTNGYTR (SEQ ID NO. 1) | 542.8 | 404.7 | 3.405 | −20 | −18 | −15 |
| IYPTNGYTR (SEQ ID NO. 1) | 542.8 | 277.2 | 3.405 | −20 | −16 | −30 |
| FTISADTSK (SEQ ID NO. 3) | 485.2 | 822.4 | 3.635 | −18 | −18 | −32 |
| FTISADTSK (SEQ ID NO. 3) | 485.2 | 721.4 | 3.635 | −11 | −18 | −26 |
| FTISADTSK (SEQ ID NO. 3) | 485.2 | 608.3 | 3.635 | −18 | −19 | −32 |
| FTISADTSK (SEQ ID NO. 3) | 485.2 | 521.3 | 3.635 | −18 | −19 | −38 |
| FTISADTSK (SEQ ID NO. 3) | 485.2 | 335.2 | 3.635 | −18 | −24 | −24 |
| GLEWVAR (SEQ ID NO. 6) | 415.7 | 660.3 | 4.077 | −30 | −15 | −24 |
| GLEWVAR (SEQ ID NO. 6) | 415.7 | 531.3 | 4.077 | −30 | −16 | −40 |
| GLEWVAR (SEQ ID NO. 6) | 415.7 | 345.2 | 4.077 | −16 | −17 | −24 |
| GLEWVAR (SEQ ID NO. 6) | 415.7 | 246.2 | 4.077 | −30 | −18 | −17 |
| NTAYLQMNSLR (SEQ ID NO. 7) | 655.8 | 1095.6 | 4.144 | −24 | −23 | −42 |
| NTAYLQMNSLR (SEQ ID NO. 7) | 655.8 | 1024.5 | 4.144 | −24 | −22 | −40 |
| NTAYLQMNSLR (SEQ ID NO. 7) | 655.8 | 861.5 | 4.144 | −24 | −22 | −32 |
| NTAYLQMNSLR (SEQ ID NO. 7) | 655.8 | 748.4 | 4.144 | −24 | −23 | −28 |
| NTAYLQMNSLR (SEQ ID NO. 7) | 655.8 | 620.3 | 4.144 | −24 | −23 | −32 |
| NTAYLQMNSLR (SEQ ID NO. 7) | 655.8 | 489.3 | 4.144 | −24 | −23 | −25 |
| NTAYLQMNSLR (SEQ ID NO. 7) | 655.8 | 375.2 | 4.144 | −24 | −22 | −19 | wherein the porous body has an average pore diameter in a range of 10 nm-200 nm, the nanoparticles have an average particle size in a range of 50 nm-500 nm, provided that the average particle size of the nanoparticles is larger than the average pore diameter of the porous body, the monoclonal antibody is trastuzumab or trastuzumab-DM1, and the peptide fragment includes the amino acid sequence of SEQ ID No: 1, 3, 6 and/or 7.

2. A method of detecting a monoclonal antibody, comprising:

bringing into contact in a liquid a porous body having pores in which the monoclonal antibody is immobilized and nanoparticles on which a protease is immobilized such that a selective proteolysis of the monoclonal antibody occurs; and detecting a peptide fragment by multiple reaction monitoring under conditions described below using liquid chromatography-mass spectrometry,

| Bevacizumab quantitation peptide and its mass spectrometry information | | | | | |
|---|---|---|---|---|---|
| Peptide Sequence | Parent ion m/z | Fragment ion m/z | Retention time [minutes] | Q1 Pre Bias [V] | Collision Energy [V] | Q3 Pre Bias [V] |
| STAYLQMNSLR (SEQ ID NO. 9) | 642.3 | 1024.5 | 4.147 | −24 | −25 | −40 |
| STAYLQMNSLR (SEQ ID NO. 9) | 642.3 | 861.5 | 4.147 | −24 | −25 | −20 |
| STAYLQMNSLR (SEQ ID NO. 9) | 642.3 | 748.4 | 4.147 | −24 | −22 | −28 |
| STAYLQMNSLR (SEQ ID NO. 9) | 642.3 | 620.3 | 4.147 | −24 | −24 | −32 |
| STAYLQMNSLR (SEQ ID NO. 9) | 642.3 | 489.3 | 4.147 | −24 | −22 | −25 |
| STAYLQMNSLR (SEQ ID NO. 9) | 642.3 | 375.2 | 4.147 | −24 | −22 | −27 |
| FTFSLDTSK (SEQ ID NO. 10) | 523.3 | 898.5 | 4.432 | −38 | −20 | −34 |
| FTFSLDTSK (SEQ ID NO. 10) | 523.3 | 797.4 | 4.432 | −38 | −18 | −30 |
| FTFSLDTSK (SEQ ID NO. 10) | 523.3 | 650.3 | 4.432 | −38 | −19 | −34 |
| FTFSLDTSK (SEQ ID NO. 10) | 523.3 | 563.3 | 4.432 | −38 | −22 | −40 |
| FTFSLDTSK (SEQ ID NO. 10) | 523.3 | 450.2 | 4.432 | −20 | −23 | −30 |
| FTFSLDTSK (SEQ ID NO. 10) | 523.3 | 335.2 | 4.432 | −20 | −25 | −24 |
| FTFSLDTSK (SEQ ID NO. 10) | 523.3 | 399.2 | 4.432 | −38 | −17 | −11 |
| FTFSLDTSK (SEQ ID NO. 10) | 523.3 | 249.1 | 4.432 | −38 | −17 | −17 |
| VLIYFTSSLHSGVPSR (SEQ ID NO. 11) | 588.3 | 832.4 | 4.515 | −22 | −19 | −30 |
| VLIYFTSSLHSGVPSR (SEQ ID NO. 11) | 588.3 | 775.9 | 4.515 | −22 | −18 | −28 |
| VLIYFTSSLHSGVPSR (SEQ ID NO. 11) | 588.3 | 719.4 | 4.515 | −22 | −18 | −26 |
| VLIYFTSSLHSGVPSR (SEQ ID NO. 11) | 588.3 | 637.8 | 4.515 | −22 | −18 | −24 |
| VLIYFTSSLHSGVPSR (SEQ ID NO. 11) | 588.3 | 564.3 | 4.515 | −22 | −22 | −20 |
| VLIYFTSSLHSGVPSR (SEQ ID NO. 11) | 588.3 | 602.3 | 4.515 | −22 | −28 | −22 |
| VLIYFTSSLHSGVPSR (SEQ ID NO. 11) | 588.3 | 359.2 | 4.515 | −22 | −26 | −26 |
| VLIYFTSSLHSGVPSR (SEQ ID NO. 11) | 588.3 | 213.2 | 4.515 | −22 | −20 | −23 | wherein the porous body has an average pore diameter in a range of 10 nm-200 nm, the nanoparticles have an average particle size in a range of 50 nm-500 nm, provided that the average particle size of the nanoparticles is larger than the average pore diameter of the porous body, the monoclonal antibody is bevacizumab, and the peptide fragment includes the amino acid sequence of at least one of SEQ ID No: 9-11.

3. A method of detecting a monoclonal antibody, comprising:
bringing into contact in a liquid a porous body having pores in which a monoclonal antibody is immobilized and nanoparticles on which a protease is immobilized such that a selective proteolysis of the monoclonal antibody occurs; and detecting a peptide fragment by multiple reaction monitoring under conditions described below using liquid chromatography-mass spectrometry,

| Rituximab quantitation peptide and its mass spectrometry information | | | | | |
|---|---|---|---|---|---|
| Peptide Sequence | Parent ion m/z | Fragment ion m/z | Retention time [minutes] | Q1 Pre Bias [V] | Collision Energy [V] | Q3 Pre Bias [V] |
| ATLTADK (SEQ ID NO. 13) | 360.2 | 648.4 | 2.809 | −26 | −14 | −24 |
| ATLTADK (SEQ ID NO. 13) | 360.2 | 547.3 | 2.81 | −13 | −13 | −20 |
| ATLTADK (SEQ ID NO. 13) | 360.2 | 434.2 | 2.81 | −26 | −16 | −22 |
| ATLTADK (SEQ ID NO. 13) | 360.2 | 333.2 | 2.81 | −26 | −19 | −24 |
| ATLTADK (SEQ ID NO. 13) | 360.2 | 262.1 | 2.81 | −13 | −21 | −29 |
| LASGVPVR (SEQ ID NO. 15) | 399.7 | 685.4 | 3.426 | −29 | −17 | −34 |
| LASGVPVR (SEQ ID NO. 15) | 399.7 | 614.4 | 3.426 | −30 | −16 | −32 |
| LASGVPVR (SEQ ID NO. 15) | 399.7 | 527.3 | 3.426 | −15 | −16 | −38 |
| LASGVPVR (SEQ ID NO. 15) | 399.7 | 371.2 | 3.426 | −15 | −17 | −28 |
| ATSNLASGVPVR (SEQ ID NO. 16) | 586.3 | 912.5 | 3.728 | −22 | −25 | −34 |
| ATSNLASGVPVR (SEQ ID NO. 16) | 586.3 | 685.4 | 3.728 | −22 | −23 | −38 |
| ATSNLASGVPVR (SEQ ID NO. 16) | 586.3 | 614.4 | 3.728 | −22 | −25 | −24 |
| ATSNLASGVPVR (SEQ ID NO. 16) | 586.3 | 527.3 | 3.728 | −22 | −25 | −40 |
| ATSNLASGVPVR (SEQ ID NO. 16) | 586.3 | 470.3 | 3.728 | −22 | −19 | −17 |
| ATSNLASGVPVR (SEQ ID NO. 16) | 586.3 | 371.2 | 3.728 | −22 | −17 | −27 | wherein the porous body has an average pore diameter in a range of 10 nm-200 nm, the nanoparticles have an average particle size in a range of 50 nm-500 nm, provided that the average particle size of the nanoparticles is larger than the average pore diameter of the porous body, the monoclonal antibody is rituximab, and the peptide fragment includes the amino acid sequence of SEQ ID No: 13, 15 and/or 16.

4. The method according to claim 3, wherein the peptide fragment includes the amino acid sequence of SEQ ID No: 13.

5. The method according to claim 3, wherein the peptide fragment includes the amino acid sequence of SEQ ID No: 15.

6. The method according to claim 3, wherein the peptide fragment includes the amino acid sequence of SEQ ID No: 16.

7. The method according to claim 1, wherein the peptide fragment includes the amino acid sequence of SEQ ID No: 1.

8. The method according to claim 1, wherein the peptide fragment includes the amino acid sequence of SEQ ID No: 3.

9. The method according to claim 1, wherein the peptide fragment includes the amino acid sequence of SEQ ID No: 6.

10. The method according to claim 1, wherein the peptide fragment includes the amino acid sequence of SEQ ID No: 7.

11. The method according to claim 2, wherein the peptide fragment includes the amino acid sequence of SEQ ID No: 9.

12. The method according to claim 2, wherein the peptide fragment includes the amino acid sequence of SEQ ID No: 10.

13. The method according to claim 2, wherein the peptide fragment includes the amino acid sequence of SEQ ID No: 11.

* * * * *